United States Patent [19]

Huang et al.

[11] Patent Number: 5,082,849

[45] Date of Patent: Jan. 21, 1992

[54] QUINOLINYL-BENZOPYRAN DERIVATIVES AS ANTAGONISTS OF LEUKOTRIENE D4

[76] Inventors: Fu-Chich Huang, 1333 Tanglewood Dr., Gwynedd, Pa. 19436; Henry F. Campbell, 767 Hazelwood, North Wales, Pa. 19454; Keith S. Learn, Box 2, Gottschall Rd., Perkiomenville, Pa. 18074

[21] Appl. No.: 659,403

[22] PCT Filed: Jul. 9, 1990

[86] PCT No.: PCT/US90/03847

§ 371 Date: Mar. 8, 1991

§ 102(e) Date: Mar. 8, 1991

[87] PCT Pub. No.: WO91/01123

PCT Pub. Date: Feb. 7, 1991

Related U.S. Application Data

[63] Continuation-in-part of Ser. No. 379,528, Jul. 13, 1989, Pat. No. 4,977,162.

[51] Int. Cl.$^5$ .............. C07D 405/12; A61K 31/47
[52] U.S. Cl. .................. 514/314; 546/152; 546/172; 546/174; 546/176; 546/178; 546/180
[58] Field of Search ............. 514/314; 546/172, 174, 546/176, 178

[56] References Cited

U.S. PATENT DOCUMENTS

| | | | |
|---|---|---|---|
| 4,282,230 | 8/1981 | Hoehn | 514/314 |
| 4,661,499 | 4/1987 | Young | 514/311 |
| 4,769,461 | 9/1988 | Musser | 546/152 |

Primary Examiner—David B. Springer

[57] ABSTRACT

This invention relates to certain quinolinyl-benzopyran compounds and their use as valuable pharmaceutical agents, particularly as lipoxygenase inhibitors and/or leukotriene antagonists and/or mediator release inhibitors possessing anti-inflammatory and anti-allergic properties.

13 Claims, No Drawings

QUINOLINYL-BENZOPYRAN DERIVATIVES AS ANTAGONISTS OF LEUKOTRIENE D4

This application is a continuation-in-part of co-pending application U.S. Ser. No. 379,528, filed July 13, 1989, now U.S. Pat. No. 4,977,162.

FIELD OF THE INVENTION

Leukotrienes (LT) are metabolites of arachidonic acid formed by oxygenation by a novel lipoxygenase specific for the C-5 position of the arachidonic acid. This forms 5-hydroperoxytetraenoic acid (5-HPETE). The latter is further transformed into an unstable epoxide intermediate leukotriene $A_4$. The $LTA_4$ can then form the peptidoleukotrienes. The $LTC_4$ is formed by glutathione addition with 5-transferase. $LTC_4$ may then be metabolized to $LTD_4$ and $LTE_4$ by successive elimination of a δ-glutamyl residue and glycine. This pathway has received much attention during the past few years and means have been sought as to how leukotriene antagonist properties could be established, i.e., researchers have been seeking a means to antagonize one or more of the arachidonic acid metabolites known as the peptido-leukotrienes $LTC_4$, $LTD_4$ and $LTE_4$. These are also known as the cysteinyl leukotrienes and they primarily affect smooth muscle and other cells having cotractile capacity. In general these $C_4$, $D_4$ and $E_4$ leukotrienes have been shown to play a key role in hypersensitivity reactions. They have bronchospastic action and activate airway smooth muscle. Inhalation studies on healthy volunteers and asthmatic subjects have corroborated that $LTC_4$ and $LTD_4$ are potent inducers of airway obstruction such as stimulation of mucous secretion. In addition, asthmatics are hyperreactive to inhaled leukotrienes which are involved with the pathogenesis of asthma such as allergic pulmonary disorders of asthma, hay fever and allergic rhinitis. These peptido-leukotrienes also are powerful spasmogens, increase vascular permeability and are involved with the pathogenesis of certain inflammatory diseases such as bronchitis, ectopic and atopic eczema and psoriasis. They are the bioactive components of Slow-Reacting-Substance of Anaphylaxis (SRS-A). In addition, $LTC_4$, $LTD_4$ and $LTE_4$ may also decrease blood pressure by an action on the heart, because cysteinyl leukotrienes reduce myocardial contractility and coronary blood flow. The hypotensive phase is usually preceded by an initial pressor effect which is primarily a consequence of generalized arteriolar constriction.

Emphasis has been directed for several years to the synthesis of compounds which are $LTD_4$ antagonists. It is thought that such compounds would be of significant value in the regulation of coronary flow rate and contractile force of the heart. They would also be useful in the treatment of hypersensitivity and bronchospastic disorders involving smooth muscle such as asthma, hay fever and allergic rhinitis. It is further thought that inflammatory conditions such as bronchitis, ectopic and atopic eczema and psoriasis could be controlled.

There is currently a number of Leukotriene $D_4$ antagonists being developed. These include a number of compounds contained in patent applications which are assigned to the same assignee as the present invention. These include U.S. Pat. Nos.: 4,920,132, 4,920,130, 4,920,133, 4,918,081 and 4,920,131.

SUMMARY OF THE INVENTION

This invention relates to quinolinyl-benzopyran compounds having $LTD_4$ antagonist properties and to therapeutic compositions and methods for the treatment of disorders which result from $LTD_4$ activity. In general, the compounds of this invention can be described by general Formula I

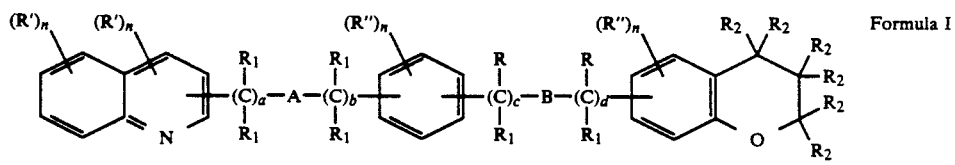

Formula I where: A is O, S,

or a carbon-carbon single
B is a carbon-carbon single bond, O, S, SO, $SO_2$, $NR_1$,

D is O, S, $NR_1$,

or a carbon-carbon single bond;
E is a carbon-carbon single bond or

a is 0–1; b is 0–1; c is 0–3; d is 0–3; e is 0–3;
f is 0–3; n is 0–2;
R' is independently hydrogen, alkyl, hydroxy, alkoxy, carboxy, carbalkoxy, halo, nitro, haloalkyl, cyano or acyl;
R" is independently hydrogen, hydroxy, alkoxy, halo, haloalkyl, or $-(CH_2)_x$-M-$(CH_2)_y$-X;
$R_1$ is independently hydrogen, alkyl or aralkyl; $R_2$ is hydrogen or $R_3$;
vicinal $R_2$ groups may form a double bond;
geminal $R_2$ groups may form a keto group; $R_3$ is

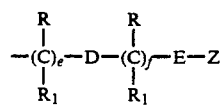

provided at least one $R_2$ group and no more than two non-geminal $R_2$ groups are $R_3$ at the same time;
R is independently hydrogen or $-(CH_2)_x$-M-$(CH_2)_y$-X provided M and A or B are not geminal oxygen atoms;
x is 0–3; y is 0–3;
M is a carbon-carbon single bond, O, S or $NR_1$;
X is hydrogen, alkyl, alkenyl, cycloalkyl, aryl, aralkyl, hydroxy, alkoxy, aralkoxy, amino, mono- and di-alkylamino, aralkylamino, acylamino, $-CONR_1R_1$, $-COOR$, CN, tetrazolyl,

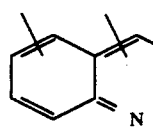 or $-CNHSO_2R_4$ where $R_4$ is hydrogen, alkyl, haloalkyl, phenyl or benzyl;
vicinal R groups together may be $-(CH_2)_y$- where y is 1–4, thus forming a 3–6 membered ring;
geminal $R_1$ and R groups may together form a spiro substituent, $-(CH_2)_z$-, where z is 2–5;
geminal $R_1$ or $R_1$ and R groups may together form an alkylidenyl substituent,

Z is $-COOR_1$, $-CN$,

where $R_4$ is as described above,

$-OR_1$, tetrazolyl, substituted tetrazolyl where the substituent may be alkyl, carboxyalkyl or carbalkoxyalkyl or

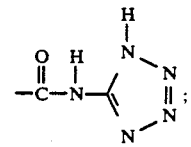

or a pharmaceutically acceptable salt thereof.

The compounds of Formula I contain at least three aromatic rings. For the purposes to this invention these may be designated as shown in Formula II. The substitution pattern of these rings along the chain with respect to each other is as follows.

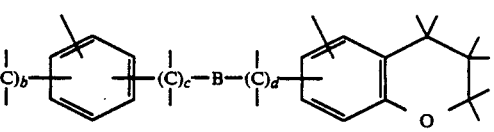

Formula II

Ring I     Ring II     Ring III

The substitution pattern of the quinoline ring, that is Ring I, is preferably at the 2-position for extending the side chain. As this side chain containing A progresses from the quinoline ring to the phenyl ring, designated as Ring II, this phenyl ring may be substituted by this chain in the ortho, meta or para positions of this phenyl ring. As the chain containing B progresses from the phenyl ring to the bicyclic benzopyran ring, designated as Ring III, this chain may originate at the ortho, meta or para positions of the phenyl ring and terminate at the 5, 6, 7 or 8 positions of the benzopyran ring. Further, the chain containing D may be substituted at the 2, 3 or 4 position of the benzopyran ring depending on the position of the keto group.

The preferred substitution pattern for Ring II is meta or para, that is:

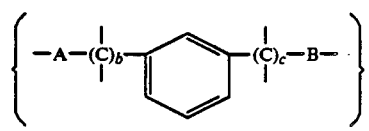 IIIa or

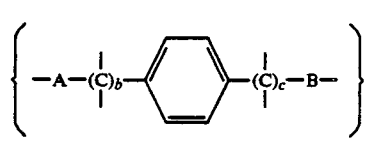 IIIb

The preferred benzopyran ring systems, that is Ring III of Formula II are the chromone and coumarin rings.

Ring III may be substituted equally in the two or three positions when the benzopyran ring is a chromone:

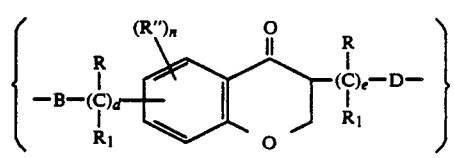 IVa

-continued
or

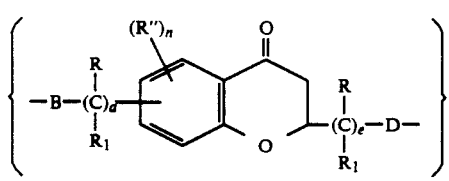
IVb

Substitution is preferably at the three position when the benzopyran ring is a coumarin:

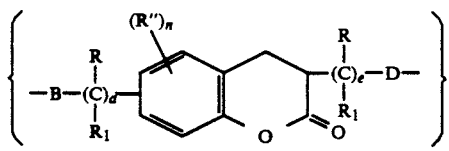
IVc

Further preferred compounds of this invention are described by Formula I where one of R and/or R" is -(CH$_2$)$_x$-M-(CH$_2$)$_y$-X and X is —CONR$_1$R$_1$, —COOR$_1$, —CN, tetrazolyl,

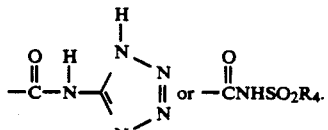

The more preferred compounds are those where A and B are O, S,

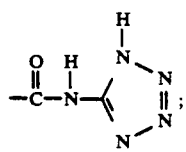

or a carbon-carbon single bond;
Z is —COOR , —CON(R$_1$)$_2$, tetrazolyl or

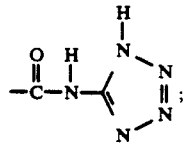

and R and R" are as described above.

In certain preferred compounds the molecule may contain what could be considered to be two side chains which are formed from R and/or R" moieties in combination with the -(C)$_e$-D-(C)$_f$-E-Z portion of the molecule or when e and f are both O and D and E are both carbon-carbon single bonds then the two side chains are formed from any combination of R and R" moieties. It is still preferred that these side chains contain acidic and/or basic functions. This will become more evident as the invention is described in greater detail.

In addition, the present invention relates to the method of using these compounds as lipoxygenase inhibitors and/or leukotriene antagonists possessing antiinflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl etc.

"Alkoxy" refers to a loweralkyl-0-group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aryl" means aromatic hydrocarbon radical such as phenyl, substituted phenyl, naphthyl or substituted naphthyl where the substituents may be independently one or more R' groups. The preferred aryl groups are phenyl and tolyl.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic group derived from an organic acid by removal of its hydroxyl group. Preferred acyl groups are acetyl, propionyl, benzoyl, etc.

"Halo" means a halogen. Preferred halogens include, chloride, bromide and fluoride. The preferred haloalkyl group is trifluoromethyl.

The compounds of this invention may be prepared in segments as is common to a long chain molecule. Thus it is convenient to synthesize these molecules by employing condensation reactions at the A, B and D cites of the molecule. For this reason the present compounds may be prepared by art recognized procedures from known compounds or readily preparable intermediates. Exemplary general procedures are as follows. For simplicity, the following procedures are shown using where the bicyclic ring is a chromone. These procedures are also intended for all the bicyclic rings of this invention, such as coumarin. Thus in order to prepare the chromone compounds, the following reactions may be employed:

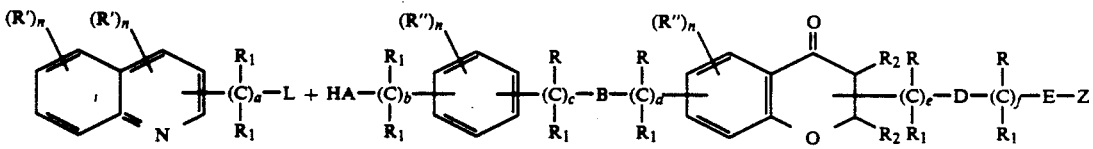

-continued

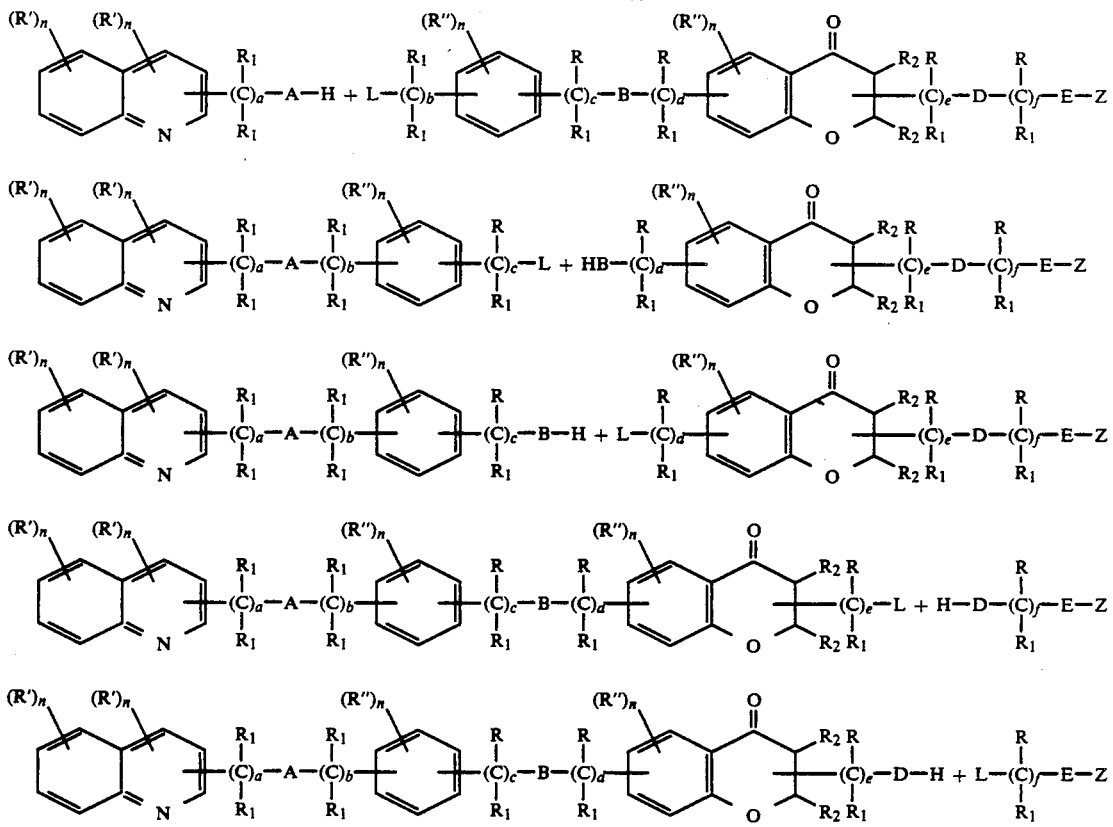

where
R, R', R", $R_1$, $R_2$, a, b, c, d, e, f, n, A, and D are as defined above;
B is O or S;
E is a carbon-carbon single bond;
Z is

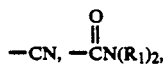

—$COOR_1$ or tetrazolyl; and L is a leaving group, such as halo, tosylate, or mesylate.

Where B is O or S, any base normally employed to deprotonate an alcohol or thiol may be used, such as sodium hydride, sodium hydroxide, triethyl amine, sodium bicarbonate or diisopropyl/ethylamine.

Reaction temperatures are in the range of room temperature to reflux and reaction times may vary from 2 to 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where B is SO or $SO_2$ then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% $H_2O_2$.

Those compounds where B is

may be prepared by the following reaction sequence:

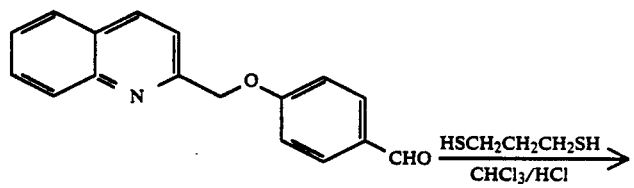

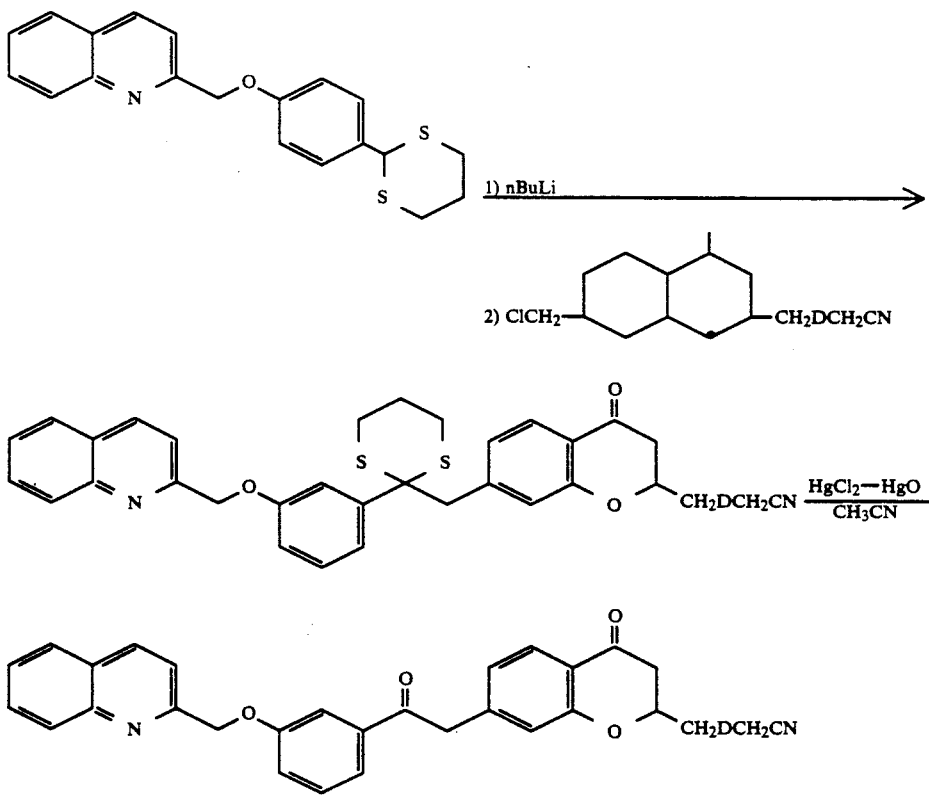

Condensation of the aldehyde with 1,3-propanedithiol results in the dithiane compound. This may be carried out in chloroform at reduced temperatures (−20° C.) while bubbling HCl gas into the reaction mixture. The dithiane compound is then treated with N-butyllithium in nonpolar solvent at −78° C. and then reacted with the substituted chromonylmethyl chloride. This results in addition of the Ring III to the molecule. The dithiane moiety is then treated with a mercuric chloride - mercuric oxide mixture to form the complex which is then split off leaving the desired compound.

Corresponding compounds may be prepared using the appropriately substituted chromonyl chloride:

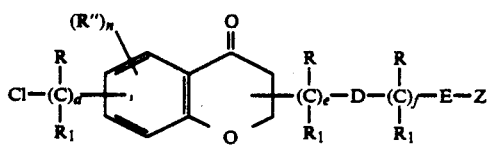

Wittig condensation also may take place at the B position of the molecule of Formula I as follows:

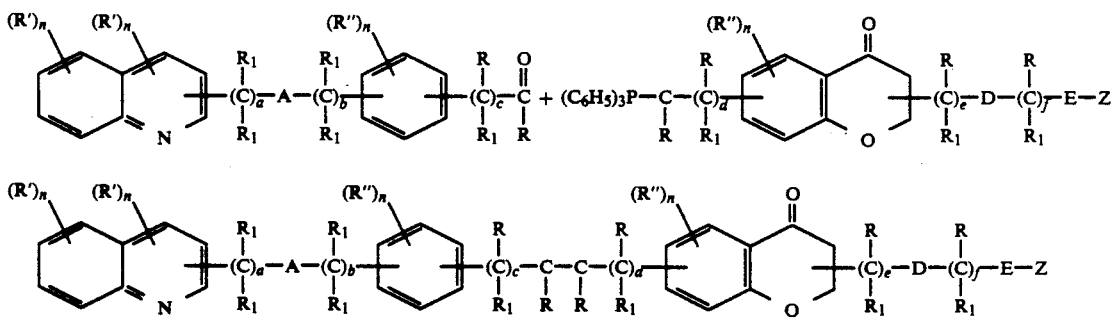

This may be carried out using normal Wittig reaction conditions. When the appropriate aldehyde or ketone is reacted with a Wittig reagent then condensation results in formation of the double bond. This may then be reduced catalytically by known procedures such as Pd/C or any other suitable hydrogenating condition.

The Wittig reagent is prepared by known art recognized procedures such as reaction of triphenyl phosphine or diethylphosphone, with a substituted alkyl bromide followed by treatment with a strong organometallic or alkoxide base such as n-BuLi or NaOH results in the desired ylide.

Of course this Wittig condensation may also take place when the Wittig reagent is formed on Ring II position of the molecule which is then condensed with the aldehyde from the benzopyran Ring III portion.

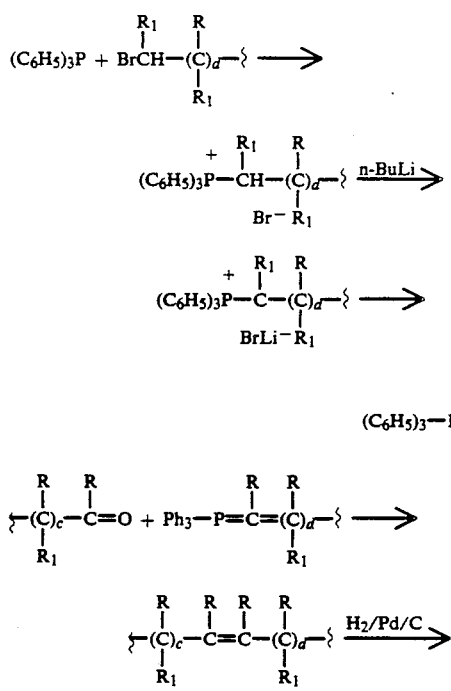
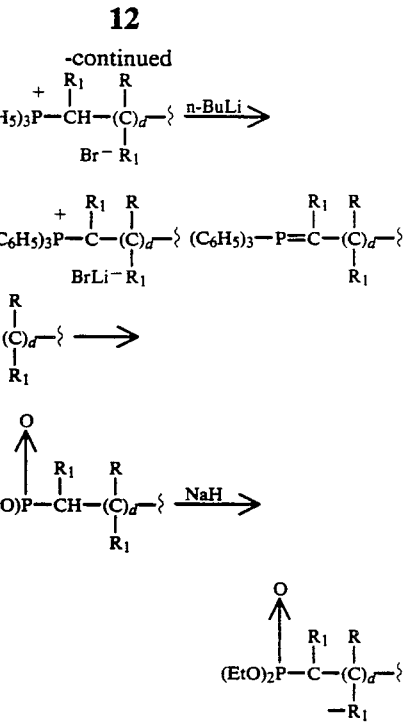
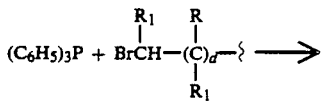
When B is
$$-\overset{R_1}{\underset{}{N}}-\overset{O}{\underset{}{C}}- \text{ or } -\overset{O}{\underset{}{C}}-\overset{R_1}{\underset{}{N}}-$$
then condensation of the acid halide with the appropriate chromonylamine will give the desired compound:
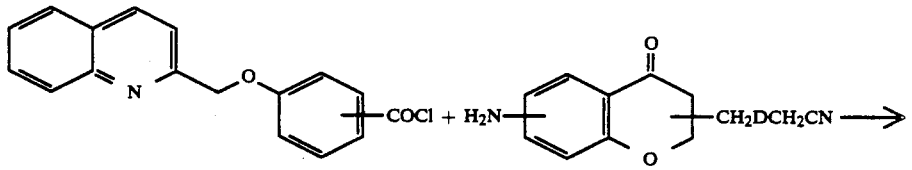
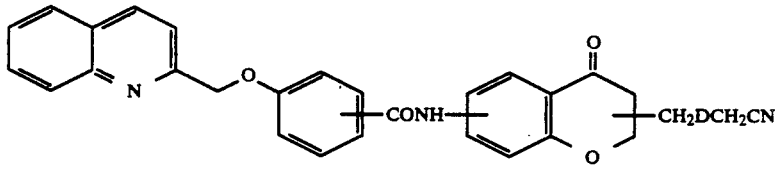
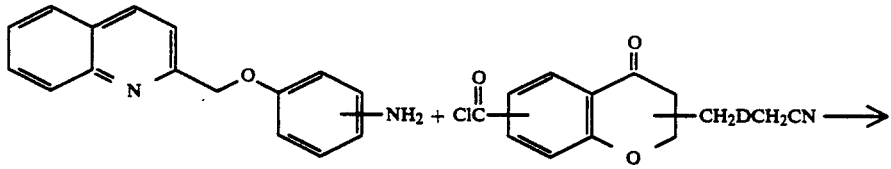
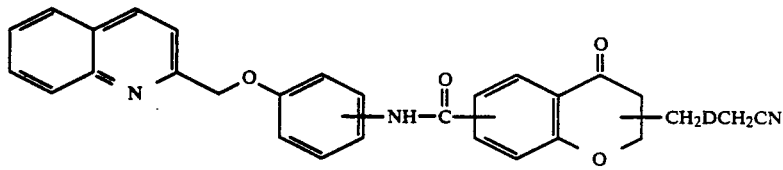
Of course, using the appropriate chromonylamine will result in the corresponding product.

Those compounds where D and/or E are

are prepared by reacting the appropriate aldehyde or ketone with a substituted Wittig reagent of the formula:

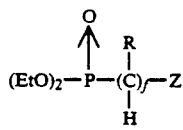

where Z is cyano or carbalkoxy.

The tetrazole may be formed from the nitrile at various stages of the synthesis by treatment with hydrazoic acid formed in situ from sodium azide and an acid.

The products of this invention may be obtained as racemic mixtures of their dextro and levorotatory isomers since at least one asymmetric carbon atom may be present. When two asymmetric carbon atoms are present the product may exist as a mixture of two diastereomers based on syn and anti configurations. These diastereomers may be separated by fractional crystallization. Each diastereomer may then be resolved into dextro and levorotatory optical isomers by conventional methods. Chromatographic methods may also be used.

Resolution may best be carried out in the intermediate stage where it is convenient to combine the racemic compound with an optically active compound by salt formation, ester formation, or amide formation to form two diasteromeric products. If an acid is added to an optically active base, then two diastereomeric salts are produced which posses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are IO pharmaceutically acceptable. Basic salts for pharmaceutical use are the Na, K, Ca and Mg salts.

Various substituents on the compounds of this invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure - (Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen - 5% carbon dioxide and maintained at 37.C. The assay buffer has been made as follows: for each liter of buffer the following are added to approximately 800 ml of water distilled in glass-6.87g NaCl, 0.4g MgSO$_4$ 7H$_2$O, and 2.0g D-glucose. Then a solution of 0.368g CaCl$_2$ H$_2$O in 100 ml glass-distilled water is slowly added to the buffer. Sufficient water is added to adjust the volume to 1 liter, and the solution is aerated with 95% oxygen - 5% carbon dioxide. Usually 10 liters of buffer are used for an experiment with 4 tissues. After the tissues have been repeatedly washed and allowed to equilibrate in the tissue bath, they are challenged with 1M histamine. After maximum contractions have been obtained, the tissues are washed, and allowed to relax back to baseline tension. This histamine challenge procedure is repeated at least 1 to 2 more times to obtain a repeatable control response. The average response to 1M histamine for each tissue is used to normalize all other challenges.

Responses of each tissue to a predetermined concentration of leukotriene are then obtained. Usually test compounds are examined initially at 30 M on resting tension of the tissues without any added agonist or antagonist to determine if the compound has any possible intrinsic activity. The tissues are washed and the test compound is added again. Leukotriene is added after the desired preincubation time. The intrinsic activity of the compounds, and their effect on leukotriene-induced contractions are then recorded.

The results of this test for the compounds of the this invention indicates that these compounds are considered to be useful leukotriene antagonists.

Inhibitions of ($^3$H)-LTD$_4$ Binding Membranes from Guinea Pig Lung.

A. Preparation of the Crude Receptor Fraction:

This procedure was adapted from Mong et al. (1984). Male guinea pigs are sacrificed by decapitation and their lungs are quickly removed and placed in a beaker containing ice-cold homogenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at 1000 xg for 10 minutes (e.g. 3500 RPM, SS-34 Rotor). The supernate is filtered through two layers of cheese cloth and centrifuged at 30,000 xg for 30 minutes (e.g. 18,500 RPM SS-34 Rotor), after which the resulting pellet is resuspended in 20 Volumes of assay buffer by hand homogenization using a Dounce homogenizer. The final pellet is resuspended in 10 volumes of assay buffer and kept at 4° C. until use.

B. Binding Assay:

Each assay tube (16×100 mm) contains the following:

490 μL Assay Buffer
10 μL Test compound or solvent
100 μL $^3$H-LTD$_4$ (ca. 17,500 DMP)
400 μL Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to equilibrate for 4–6 hours, the radioactivity is counted with a liquid scintillation counter appropriately set for tritium.

The required control assay tubes include the following:

(a) Total Binding: No test compound is added; buffer is substituted.
(b) Non-Specific Binding: Non-labeled ligand is added at a concentration of 1M.
(c) Solvent Controls If test compound is dissolved in a solvent, controls for both Total Binding and Non-Specific Binding containing solvent but no compounds are required.

The results of this test indicate that compounds of this invention exhibit valuable properties which are useful in the treatment of inflammatory conditions and allergic responses.

Preferred compounds of the present invention also show activity as inhibitors of mediator release from passively sensitized rat mast cells (RMC), making them useful in the treatment of allergy and asthma. Thus, preferred compounds possess dual activity as mediator release inhibitors and LTD$_4$ antagonists. Standard testing procedures to measure histamine release when mast cells are challenged with antigen may be found in the following reference: Kusner, et.al., J. Pharmacol. and Exp. Ther. 184, 41(1973).

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable us include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples:

EXAMPLE 1

2-(3-hydroxyphenoxy)methylquinoline

A mixture (0.06 moles) of 2-chloromethylquinoline hydrochloride, (0.06 moles) of 1,3-benzenediol and 18 g of potassium carbonate in 50 ml of dimethylformamide is heated at 70°,C. overnight. The reaction mixture is poured into water, and the precipitated product is collected, filtered and dried to give 2-(3-hydroxyphenoxy)-methylquinoline having an m.p. of 151°–53° C.

EXAMPLE 2

When 2-chloromethylquinoline hydrochloride of Example 1 above is replaced by the quinoline compounds of Table I below, then the corresponding product is obtained.

TABLE I 2-bromomethylquinoline
2-(1-chloroethyl)quinoline
2-(2-chloroethyl)quinoline
2-(2-bromoethyl)quinoline
3-chloromethylquinoline
4-chloromethylquinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline
2-chloromethyl-7-chloroquinoline
2-chloromethyl-7-bromoquinoline
2-chloromethyl-7-nitroquinoline
2-chloromethyl-7-methylquinoline

EXAMPLE 3

When 1,3-benzenediol of Example 1 above is replaced by the compounds of Table II below, then the corresponding product is obtained.

TABLE II 1,2-benzenediol
1,4-benzenediol
2-mercaptophenol
3-mercaptophenol
4-mercaptophenol
1,3-dimercaptobenzene
1,4-dimercaptobenzene
2-methylresorcinol
5-methylresorcinol
5-methoxyresorcinol
5-methyl-1,4-dihydroxybenzene
methyl salicylate
methyl-3-hydroxybenzoate
methyl-4-hydroxybenzoate
3-hydroxybenzaldehyde
2-hydroxybenzaldehyde
4-hydroxybenzaldehyde

EXAMPLE 4

When 1,3-benzenediol of Example 1 is replaced by the compounds of Table III, then the corresponding products are obtained.

TABLE III 3-hydroxybenzylalcohol
3-hydroxyethylphenol
4-hydroxybenzylalcohol
4-hydroxyethylphenol
2-hydroxy-α-ethylbenzylalcohol
2-hydroxy-α-propylbenzylalcohol
3-hydroxy-α-methylbenzylalcohol
3-hydroxy-α-ethylbenzylalcohol
3-hydroxy-α-propylbenzylalcohol
4-hydroxy-α-methylbenzylalcohol
4-hydroxy-α-ethylbenzylalcohol
4-hydroxy-α-propylbenzylalcohol

EXAMPLE 5

When the compounds of Table I, Example 2 are reacted with the compounds of Table II, Example 3 under the conditions of Example 1, then the corresponding products are obtained.

EXAMPLE 6

When the compounds of Table I, Example 2 are reacted with the compounds of Table III, Example 4, the corresponding products are obtained.

EXAMPLE 7

2-(3-hydroxymethylphenoxy)methylquinoline 20.0 g (93.5 mmoles) of 2-chloromethylquinoline hydrochloride, 11.6g (93.5 mmoles) of 3-hydroxybenzylalcohol and 7.48g (186.42 mmoles) of powdered sodium hydroxide are combined in 56 ml of dimethylsulfoxide. After stirring room temperature for 24 hours the mixture is poured into ice-water and the resulting solid is collected and dried to give 25.6g of 2-(3-hydroxymethylphenoxy)methylquinoline.

EXAMPLE 8

When the compounds of Table I, Example 2 are reacted with the compounds of Table II, Example 3 under the conditions of Example 7, the corresponding products are obtained.

EXAMPLE 9

When the compounds of Table I, Example 2 are reacted with the compounds of Table III, Example 4 under the conditions of Example 7, the corresponding products are obtained.

EXAMPLE 10

2-(3-chloromethylphenoxy)methylquinoline 25.6g (93.5 mmoles) of 2-(3-hydroxymethylphenoxy)methylquinoline is dissolved in 30 ml of methylene chloride and 3 drops of dimethylformamide is added. 60.7 ml of a 2.0M solution of thionyl chloride in methylene chloride is then added dropwise at 0° C. The mixture is allowed to warm to room temperature and stirred for 5 hours. The solution is worked with sodium bicarbonate solution, dried, concentrated in vacuo and the crude product purified by silica gel HPLC to yield 12.1 g 2-(3chloromethylphenoxy)methylquinoline as a pale yellow solid.

EXAMPLE 11

When 2-(3-hydroxymethylphenoxy)methylquinoline of Example 10 above is replaced by the products of Example 6 or Example 9 above, then the corresponding products are obtained.

EXAMPLE 12

5-(7-(2-(3-quinolin-2-ylmethoxy)phenyl)ethyl)-4-oxo-4H-1-benzopyran-2-yl)tetrazole Step 1: Preparation of 2-hydroxy-4-methylacetophenone A suspension of 15g (0.100 moles) m-tolylacetate and 16 g (0.120 moles) aluminum chloride is heated at 120° C. for 20 minutes. The mixture is cooled to 0° C. and water added. The pH of the mixture is adjusted to approximately 1 using 1N hydrochloric acid and the resulting mixture extracted with ethyl acetate. The organic solution is dried, and concentrated in vacuo to give an oil which is purified by column chromatography on silica gel to give 11.9g of a light yellow oil, 2-hydroxy-4-methylacetophenone, which is used directly in the next step.

Step 2: Preparation of 2-carboethoxy-7-methyl-4-oxo-4H-1-benzopyran

A solution of 10.7g (71.25 mmoles) of 2-hydroxy-4-methylacetophenone and 31.24g (214 mmoles) of diethyloxalate in 25 ml of ethanol is added dropwise to a solution of sodium ethoxide (formed by adding 6.55g of sodium metal to 120 ml of ethanol). The mixture is refluxed for 4 hours, cooled to 0° C. and diluted with 500 ml of ether. The precipitate which forms on standing overnight is filtered off and redissolved in water and the solution acidified (pH approximately 1) with 1N hydrochloric acid. The mixture is extracted with ethyl acetate which is dried and concentrated in vacuo. The residue is dissolved in 100 ml of ethanol and 3 ml of concentrated hydrochloric acid. This solution is refluxed for 1.5 hours, then concentrated in vacuo. The residue is poured into ice water and the precipitate which formed on standing overnight is filtered off and dissolved in ethyl acetate. The ethyl acetate solution is dried and concentrated in vacuo. The residue is purified by flash column chromatography through silica gel and recrystallization from ether/hexanes to give 8.75g of 2-carboethoxy-7-methyl-4-oxo-4H-1-benzopyran as a white crystalline solid having an m.p. of 62°–4° C.

Step 3: Preparation of 2-carbamyl-7-methyl-4-oxo-4H-1-benzopyran

An excess of anhydrous ammonia gas is bubbled into a solution of 8.75g of 2-carboethoxy-7-methyl-4-oxo-4H-1-benzopyran in 100 ml of ethanol, held at 0° C., for 20 minutes. This is stirred at 0° C. for 1 hour then concentrated in vacuo. The resulting oil is triturated with ether and the resulting precipitate filtered off giving 7.09g 2-carbamyl-7-methyl-4-oxo-4H-1-benzopyran as a light yellow crystalline solid having an m.p. >300° C.

Step 4: Preparation of 2-cyano-7-methyl-4-oxo-4H-benzopyran 26.41g (17.22 mmoles) of phosphorus oxychloride is added to 100 ml dimethylformamide at 0° C. and stirred at 0° C. for 15 minutes at room temperature for 30 minutes. 7.0g (34.45 mmoles) 2-carbamyl-7-methyl-4-oxo-4H-1-benzopyran is added and the mixture stirred at room temperature overnight, then poured into ice water and is allowed to stand for 1 hour at room temperature. The resulting precipitate is filtered off, redissolved in ethyl acetate, decolorized with carbon, filtered and the filtrate concentrated in vacuo to give 4.5g of 2-cyano-7-methyl-4-oxo-4H-1-benzopyran as a crystalline solid having an m.p. of 155°–56° C.

Step 5: Preparation of 7-bromomethyl-2-cyano-4-oxo-4H-1-benzopyvran

A solution of 4.5g (24.30 mmoles) 2-cyano-7-methyl-4-oxo-4H-1-benzopyran, 4.33g (24.30 moles) on N-bromosuccinimide and 100 mg of benzoyl peroxide in 75 ml carbon tetrachloride is heated at reflux under a high intensity lamp or 4 hours. The precipitate is filtered off and filtrate concentrated in vacuo. The residue is purified by flash column chromatography through silica gel to give 3.0g 7-bromomethyl-2-cyano-4-oxo-4H-1-benzopyran as a yellow crystalline solid having an m.p. of 162°–66° C.

Step 6: Preparation of trans-(E)-2-cyano-7-(2-(3-(quinolin-2-ylmethoxy)phenyl)ethenyl)-4-oxo-4H-1-benzopyran To a suspension of 4.37g (8.30 mmoles) of 2-cyano-4-oxo-4H-1-benzopyran-7-ylmethyltriphenylphosphonium bromide (prepared from 3.0g 7-bromomethyl-2-cyano-4-oxo-4H-1-benzopyran and 2.98g triphenylphosphine refluxed in toluene for 1hour) in 100 ml of dimethyl formamide is added 0.27g (9.13 mmoles) of an 80% sodium hydride in oil dispersion. After stirring at 0° C. for 1 hour, 2.18g (8.30 mmoles) of 3-(quinolin-2-ylmethoxy)benzaldehyde in 20 ml of dimethylformamide is added and stirred for 2 hours. The mixture is poured into ice water, extracted with ethyl acetate which is dried and concentrated in vacuo. Purification by flash column chromatography through silica gel gives 1.1g trans-(E)-2-cyano-7-(2-(3-(quinolin-2- ylmethoxy)phenyl)ethenyl)-4-oxo-4H-1-benzopyran as a yellow oil, which is used directly in the next step.

Step 7: Preparation of trans-(E)-5-(7-(2-(3-(quinolin-2-ylmethoxy)phenyl)ethenyl)-4-oxo-4H-1-benzopyran-2-yl)-tetrazole A suspension of 0.90g (2.1 mmoles) of trans-(E)-2-cyano-7-(2-(3-(quinolin-2-ylmethoxy)phenyl)ethenyl)-4-oxo-4H-1-benzopyran, 0.56g (10.45 mmoles) of ammonium chloride and 0.68g (10.45 mmoles) of sodium azide in 20 ml of dimethylformamide is heated at 100° C. for 18 hours. The mixture is poured into ice water. Addition of ethyl acetate gives a precipitate which is collected and crystallized from methylene chloride/petroleum ether to give 0.7g trans-(E)-5-(7-(2-(3-(quinolin-2-ylmethoxy)phenyl)ethenyl)-4-oxo-4H-1-benzopyran-2-yl)tetrazole as a pale yellow crystalline solid having an m.p. of 148°-52° C.

Step 8: Preparation of 5-(7-(2-(3-(quinolin-2-ylmethoxy)phenyl)-ethyl)-4-oxo-4H-1-benzopyran-2-yl)tetrazole To a solution of 0.20g (0.42 mmoles) of trans-(E)-5-(7-(2-(3-(quinolin-2-ylmethoxy)phenyl)ethenyl)-4-oxo-4H-1-benzopyran-2-yl)tetrazole in 30 ml of ethanol is added 0.08g of 10% palladium on carbon and the mixture is shaken under 30 psi of hydrogen for 4 hours. The mixture is filtered and the filtrate concentrated in vacuo. The residue is crystallized from methylene chloride to give 0.12g of 5-(7-(2-(3-(quinolin-2-ylmethoxy)phenyl)ethyl)-4- oxo-4H-1-benzopyran-2-yl)tetrazole as a crystalline solid having an m.p. of 201°-5° C.

EXAMPLE 13

When the compounds of Table I, Example 2 are reacted with the benzaldehyde derivatives of Table II, Example 3 under the conditions of Example 1 or Example 7, the corresponding products are obtained.

EXAMPLE 14

When the products of Example 13 are substituted for 3-(quinoline-2-ylmethoxy)benzaldehyde in Example 12, Step 6, the corresponding products are obtained.

EXAMPLE 15

When the products of Example 14 are substituted for trans-(E)-2-cyano-7-(2-(3-(quinoline-2-ylmethoxy)phenyl)ethenyl)-4-oxo-4H-1-benzopyran in Example 12, Step 7, the corresponding products are obtained.

EXAMPLE 16

When the products of Example 15 are substituted for trans-(E)-5-7-(2-(3-(quinoline-2-ylmethoxy)phenyl)ethenyl)-4-oxo-4H-1-benzopyran-2-yl)tetrazole in Example 12, Step 8, the corresponding products are obtained.

EXAMPLE 17

5-(7-(3-(quinolin-2-ylmethoxy)benzyloxy)-4-oxo-4H-1-benzopyran-2-yl)tetrazole

Step 1: Preparation of 2-carboethoxy-7-hydroxy-4-oxo-4H1-benzopyran

A solution of 2,4-dihydroxyacetophenone (15.2g) in diethyloxalate (40 ml) is added with stirring to a solution of sodium (9.2g) in ethanol (200 ml). The mixture is then heated at 100° C. for 3.5 hours, cooled and is added to dry ether (500 ml). The mixture is allowed to sit overnight. The resulting precipitate is filtered off and dissolved in water, and the solution is neutralized with 4N hydrochloric acid and extracted with ether. The ether extracts are combined and are concentrated down in vacuo. The resulting residue is dissolved in ethanol (100ml) and concentrated hydrochloric acid is then added (2 ml). The solution is heated under reflux for 2 hours and is then concentrated in vacuo. The resulting solid is recrystallized in ethanol to give 2-carboethoxy-7-hydroxy-4-oxo-4H-1-benzopyran which is used directly in the next step.

Step 2: Preparation of 2-carbamyl-7-hydroxy-4-oxo-4H-1-benzopyran

Into a suspension of 2-carboethoxy-7-hydroxy-4-oxo-4H-1-benzopyran (34.44 mmoles) in methanol is bubbled gaseous ammonia for 0.5 hours. After 1 hour the reaction mixture is concentrated in vacuo to yield 2-carbamyl-7- hydroxy-4-oxo-4H-1-benzopyran, which is used directly in the next step.

Step 3: Preparation of 2-cyano-7-hydroxy-4-oxo-4H-1-benzopyran

To 2-carbamyl-7-hydroxy-4-oxo-4H-1-benzopyran obtained above in dimethylformamide (200 ml) at 0° C. is added dropwise phosphorus oxychloride (16.2 ml). After 24 hours, the reaction mixture is poured into ice water (600 ml) and the resulting precipitate is collected. The precipitate is boiled in hot hexane and filtered to give 2-cyano-7-hydroxy-4-oxo-4H-1-benzopyran, which is used directly in the next step.

Step 4: Preparation of 2-cyano-7-(3-(quinolin-2-ylmethoxy)benzyloxy)-4-oxo-4H-1-benzopyran To 2-cyano-7-hydroxy-4-oxo-4H-1-benzopyran (11.87 mmoles) and 2-((3-chloromethylphenoxy)methyl)quinoline (11.87 mmoles) in dimethylsulfoxide (20 ml) is added powdered sodium hydroxide (0.475g). After one week the reaction mixture is poured into ice water and the resulting precipitate collected and purified by HPLC to give 2-cyano-7-(3-(quinolin-2-ylmethoxy)benzyloxy)-4-oxo-4H-1-benzopyran which is used directly in the next step.

Step 5: Preparation of 5-(7-(3-(quinolin-2-ylmethoxy)benzyloxy)-4-oxo-4H-1-benzopyran-2yl)tetrazole 2-cyano-7-(3-(quinolin-2-ylmethoxy)benzyloxy)-4-oxo-4H-1-benzopyran (2.97 mmoles), sodium azide (965 mg), pyridine hydrochloride (1.72g) and dimethylformamide (7 ml) are combined and heated at 100° C. for 48 hours. The reaction mixture is poured into cold water and the resulting precipitate is collected. The precipitate is dissolved in hot ethanol and reprecipitated by addition of water to give 5-(7-(3-(quinolin-2-ylmethoxy)benzyloxy)-4-oxo-4H-1-benzopyran-2-yl)tetrazole which decomposes at 203° C.

EXAMPLE 18

When 2-((3-chloromethylphenoxy)methyl)quinoline in Example 17, Step 4 above, is replaced by the products of Example 11, then the corresponding products are obtained.

EXAMPLE 19

When 2-cyano-7-(3-(quinolin-2-ylmethoxy)benzyloxy)-4-oxo-4H-1-benzopyran in Example 17, Step 5 above, is replaced by the products of Example 18, then the corresponding products are obtained.

EXAMPLE 20

2-carbopropoxy-6-(3-(quinolin-2-ylmethoxy)benzyloxy)-4-oxo-4H-1-benzopyran

Step 1: Preparation of 2-hydroxy-5-(tetrahydropyran-2-yloxy)acetophenone 14.89g of 2,5-dihydroxy acetophenone, 25.18g of dihydropyran and 100 mg of p-toluenesulfonic acid are stirred together at room temperature overnight. The resulting mixture is dissolved in 1 l of ether and the ether solution washed with sodium bicarbonate solution, water and brine, then dried over sodium sulfate and concentrated in vacuo to give 2-hydroxy-5-(tetrahydropyran-2-yloxy)acetophenone as an oil, which is used directly in the next step.

Step 2: Preparation of 2-carboethoxy-6-(tetrahydropyran-2-yloxy)-4-oxo-4H-1-benzopyran The 2-hydroxy-5-(tetrahydropyran-2-yloxy)acetophenone from the above example and 91g of ethyl oxalate were combined and added to an ice cold solution of sodium ethoxide (made from 9.0g of sodium metal) in 400 ml of absolute ethanol. The solution is refluxed for 30 minutes, then concentrated in vacuo. The residue is added to a solution of 50 ml of glacial acetic acid in 1 l of water and extracted in 4×250 ml of chloroform. The combined chloroform extract is washed with sodium bicarbonate solution, brine and dried over Na$_2$SO$_4$. This was concentrated to give 2-carboethoxy-6-(tetrahydropyran-2-yloxy)-4-oxo-4H-1-benzopyran as an orange oil which is used directly in the next step.

Step 3: Preparation of 2-carboxy-6-hydroxy-4-oxo-4H-1-benzopyran

The 2-carboethoxy-6-(tetrahydropyran-2-yloxy)-4-oxo-4H-1-benzopyran from the above example is dissolved in 200 ml of glacial acetic acid to which 28 ml concentrated hydrochloric acid is added. This is refluxed for 4 hours and allowed to stand at room temperature overnight. The resulting precipitate is collected by filtration, washed with glacial acetic acid, water and absolute ethanol to give 10.28g of 2-carboxy-1-hydroxy-4-oxo-4H-1-benzopyran as a pale green solid.

Step 4: Preparation of 2-carbopropoxy-6-hydroxy-4-oxo-4H-1-benzopyran 14.14 g (49.2 mmoles) of 2-carboxy-6-hydroxy-4-oxo-4H-1-benzopyran is dissolved in 200 ml of n-propanol and 1 drop of concentrated sulfuric acid is added. The mixture is refluxed for 30 hours, concentrated. The resulting solid is suspended in water, neutralized with sodium bicarbonate and filtered, washing the solid with water, then drying. This gives 10.6g of 2-carbopropoxy-6-hydroxy-4-oxo-4H-1-benzopyran as a solid which is purified by recrystallization from n-propanol/acetone or by HPLC.

Step 5: Preparation of 2-carbopropoxy-6-(3-(quinolin-2- ylmethoxy)benzyloxy)-4-oxo-4H-1-benzopyran A mixture of 3.47g of 2-((3-chloromethylphenoxy)-methyl)quinoline, 3.04g of 2-carbopropoxy-6-hydroxy-4-oxo-4H-1-benzopyran, 1.69g of potassium carbonate and 1 ml of dimethylformamide is refluxed in 50 ml of acetone for 41 hours. The mixture is concentrated in vacuo and the residue is dissolved in water. This solution is neutralized with diluted hydrochloric acid and the resulting solid is filtered off and purified by flash silica gel chromatography in propanol-dimethylformamide to give 1.71 g of 2-carbopropoxy-6-(3-(quinolin-2-ylmethoxy)benzyloxy)-4-oxo-4H-1-benzopyran as a white solid having an m.p. of 109°-10° C.

EXAMPLE 21

Step 1: Preparation of 2-carboxy-6-(3-(quinolin-2-ylmethoxy)benzyloxy)-4-oxo-4H-1-benzopyran A mixture of 0.71g of 2-carbopropoxy-6-(3-(quinolin-2-yl-methoxy)benzyloxy)-4-oxo-4H-1-benzopyran and 0.45g of sodium bicarbonate in 20 ml of ethanol in 20 ml of water is refluxed for 1.5 hours, then stirred at room temperature overnight. The mixture was neutralized and the resulting solid is filtered off, washed with water and dried in vacuo to give 0.55g of 2-carboxy-6-(3-quinolin-2- ylmethoxy)benzyloxy)-4-oxo-4H-1-benzopyran as a light yellow solid having an m.p. of 253°-54° C.

EXAMPLE 22

Step 1: Preparation of 2-carboethoxy-7-(3-(quinolin-2-ylmethoxy)benzyloxy)-4-oxo-4H-1-benzopyran A mixture of 1.5g (6.41 mmoles) of 2-carboethoxy-7-hydroxy-4-oxo-4H-1-benzopyran, 1.82g (6.41 mmoles) of 2-3-chloromethylphenoxy)methylquinoline and 0.886 g of potassium carbonate in 12 ml of dimethylformamide and 96 ml of acetone is refluxed for 2 days, cooled, concentrated in vacuo and the residue taken up in water and is extracted into ethyl acetate. The solution is concentrated and the crude product is recrystallized from ethyl acetate to give 0.585g of 2-carboethoxy-7-(3-quinolin-2-ylmethoxy)benzyloxy)-4-oxo-4H-1-benzopyran as a pale yellow solid having an m.p. of 123°-24° C.

EXAMPLE 23

When 2-carbopropoxy-6-(3-(quinolin-2-ylmethoxy)benzyloxy)- 4-oxo-4H-1-benzopyran in Example 21 is replaced by 2-carboethoxy-7-(3-(quinolin-2-ylmethoxy)benzyloxy)-4- oxo-4H-1-benzopyran, 2-carboxy-7-(3-quinolin-2-ylmethoxy)benzyloxy)- 4-oxo-4H-1-benzopyran is obtained as a white solid having an m.p. of 201° C.

EXAMPLE 24

When 2,4-dihydroxy-3-propylacetophenone is substituted for 2,4-dihydroxyacetophenone in Example 17, Step 1, 2-carboethoxy-7-hydroxy-8-n-propyl-4-oxo-4H-1-benzopyran is obtained.

EXAMPLE 25

2-carboethoxy-6-chloro-5-hydroxy-4-oxo-4H-1-benzopyran

Step 1: Preparation of 3-chloro-2,6-dihydroxyacetophenone 6.80g of 2,6-dihydroxyacetophenone is dissolved in 100 ml of glacial acetic acid and the solution cooled to 0° C. 49.2 ml of thionyl chloride is added and the solution is refluxed for 2.5 hours. The mixture is diluted with water and the resulting solid is collected, dried and recrystallized from benzene to give 6.41 g of 3-chloro-2,6-dihydroxyacetophenone.

Step 2: Preparation of 2-carboethoxy-6-chloro-5-hydroxy4-oxo-4H-1-benzopyran

When 2,4-dihydroxyacetophenone in Example 17, Step 1 is replaced by 3-chloro-2,6-dihydroxyacetophenone, 2- carboethoxy-6-chloro-5-hydroxy-4-oxo-4H-1-benzopyran is obtained.

EXAMPLE 26

2-carboethoxy-8-methyl-4-oxo-4H-1-benzopyran

Step 1: Preparation of 2-hydroxy-3-methyl acetophenone 52.5 g of o-cresylacetate and 60 g of aluminum chloride are heated together at 165° C. for 50 minutes. The cooled mixture is poured into ice and concentrated hydrochloric acid and this mixture extracted with ether. The ether solution is washed with water, dried over sodium sulfate, then filtered through silica gel. The filtrate is evaporated, then distilled in vacuo to give 13.5 g of 2-hydroxy-3-methylacetophenone as a yellow oil which is used directly in the next step.

Step 2: Preparation of 2-carboethoxy-8-methyl-4-oxo-4H-1-benzopyran

When 2-hydroxy-4-methylacetophenone in Example 12, Step 2 is replaced by 2-hydroxy-3-methylacetophenone, 2- carboethoxy-8-methyl-4-oxo-4H-1-benzopyran is obtained.

EXAMPLE 27

2-carboethoxy-8-nitro-4-oxo-4H-1-benzopyran

Step 1: Preparation of 2-hydroxy-3-nitroacetophenone 10.0 g of 2-hydroxyacetophenone is dissolved in 60 ml of glacial acetic acid. 10.4 ml of nitric acid (specific gravity = 1.40) is then added over 2 hours at room temperature. The mixture is stirred for 17 hours, then poured onto ice and the resulting precipitate (containing both the 3- and 5-nitro isomers) collected. The isomers are separated by HPLC to give 4.0 g of 2-hydroxy-3-nitroacetophenone.

Step 2: Preparation of 2-carboethoxy-8-nitro-4-oxo-4H-1-benzopyran

When 2-hydroxy-4-methylacetophenone in Example 12, Step 2 is replaced by 2-hydroxy-3-nitroacetophenone, 2- carboethoxy-8-nitro-4-oxo-4H-1-benzopyran is obtained.

EXAMPLE 28

When 2-carboethoxy-7-hydroxy-4-oxo-4H-1-benzopyran in Example 22 is replaced by 2-carboethoxy-7-hydroxy-8-n- propyl-4-oxo-4H-1-benzopyran (from Example 24), 2- carboethoxy-8-n-propyl-7-(3-(quinolin-2-ylmethoxy)benzyloxy)- 4-oxo-4H-1-benzopyran is obtained having an m.p. of 120°-21° C.

EXAMPLE 29

When the ester in Example 21 is replaced by 2- carboethoxy-8-n-propyl-7-(3-(quinolin-2-ylmethoxy)benzyloxy)- 4-oxo-4H-1-benzopyran, 2-carboxy-8-n-propyl-7-(3-(quinolin-2-ylmethoxy)-benzyloxy)-4-oxo-4H-1-benzopyran is obtained having an m.p. of 218°-22° C.

EXAMPLE 30

2-carbopropoxy-6-chloro-5-(4-(quinolin-2-ylmethoxy)-benzyloxy)-4-oxo-4H-1-benzopyran Step 1: Preparation of 2-carboxy-6-chloro-5-hydroxy-4-oxo-4H-1-benzopyran 2-carboethoxy-6-chloro-5-hydroxy-4-oxo-4H-1-benzopyran is dissolved in glacial acetic acid and water (5:1) and the solution refluxed for 4 hours. This is cooled and the resulting solid collected and washed with water to give 2-carboxy-6-chloro-5-hydroxy-4-oxo-4H-1-benzopyran.

Step 2: Preparation of 2-carbopropoxy-6-chloro-5-hydroxy-4-oxo-4H-1-benzopyran

When the carboxylic acid of Example 20, Step 4 is replaced by 2-carboxy-6-chloro-5-hydroxy-4-oxo-4H-1-benzopyran, 2-carbopropoxy-6-chloro-5-hydroxy-4-oxo-4H-1-benzopyran, having an m.p. of 118°-20° C., is obtained.

Step 3: Preparation of 2-carbopropoxy-6-chloro-5-(4-(quinolin-2-ylmethoxy)benzyloxy)-4-oxo-4H-1-benzopyran 0.78 g of 2-(4-chloromethylphenoxy)methylquinoline, 0.76 g of 2-carbopropoxy-6-chloro-5-hydroxy-4-oxo-4H-1-benzopyran and a catalytic amount of potassium iodide are combined in 50 ml of acetone and 2 ml of dimethylformamide, and refluxed for 19 hours. The crude solid obtained on cooling is purified by flash chromatography to give 2-carbopropoxy-6-chloro-5-(4-(quinolin-2-ylmethoxy)benzyloxy) 4-oxo-4H-1-benzopyran having an m.p. of 173°-74° C.

EXAMPLE 31

2-Carboethoxy-8-(4-(quinolin-2-ylmethoxy)phenoxymethyl)-4-oxo-4H-1-benzopyran

Step 1: Preparation of 8-bromomethyl-2-carboethoxy-4-oxo-4H-1-benzopyran

When the benzopyran in Example 12, Step 5 is replaced with 2-carboethoxy-8-methyl-4-oxo-4H-1-benzopyran, 8- bromomethyl-2-carboethoxy-4-oxo-4H-1-benzopyran is obtained, which is used directly in the next step.

Step 2: Preparation of 2-carboethoxy-8-(4-(quinolin-2- ylmethoxy)phenoxymethyl)-4-oxo-4H-1-benzopyran 1.8 g of 2-(4-hydroxyphenoxy)methylquinoline, 2.2 g of 8-bromomethyl-2-carboethoxy-4-oxo-4H-1-benzopyran and 1.0 g of potassium carbonate are combined in 100 ml of acetone and refluxed for 18 hours. The mixture is cooled, diluted with ethylacetate and filtered. The filtrate is concentrated and the crude product purified by flash chromatography on silica gel in 5% ethanol in chloroform/hexane (1:1) to give 0.96 g 2-carboethoxy-8-(4- (quinolin-2-yl-methoxy)phenoxymethyl)-4-oxo-4H-1-benzopyran: m.p. 124°-27° C.

EXAMPLE 32

2-Carboxy-8-(4-(quinolin-2-ylmethoxy)phenoxymethyl)-4-oxo-4H-1-benzopyran 0.74 g of 2-carboethoxy-8-(4-(quinoline-2-ylmethoxy)phenoxymethyl)-4-oxo-4H-1-benzopyran and 0.7 g sodium bicarbonate are combined in 50 ml of ethanol and 5 ml of water. After refluxing for 1.5 hours the mixture is concentrated and the residue diluted with ether. The resulting solid is collected, suspended in water and the pH adjusted to 6 with 1 molar hydrochloric acid. The resulting solid is crystallized from aqueous acetic acid, then tetrahydrofuran/hexane to give 0.43 g 2-carboxy-8-(4- (quinolin-2-ylmethoxy)phenoxymethyl)-4-oxo-4H-1-benzopyran; m.p. 221°-24° C.

EXAMPLE 33

5-(8-(4-(quinolin-2-ylmethoxy)phenoxymethyl)-4-oxo-4H-1-benzopyran-2-yl)tetrazole Step 1: Preparation of 2-carbamyl-8-methyl-4-oxo-4H-1-benzopyran 3.4 g of 2-carboethoxy-8-methyl-4-oxo-4H-1-benzopyran is dissolved in 150 ml of methanol and, while cooling in an ice bath, anhydrous ammonia is bubbled in for 10 minutes, during which time a solid is formed. This solid is collected, worked with methanol and dried to give 2.65 g of 2-carbamyl-8-methyl-4-oxo-4H-1-benzopyran.

Step 2: Preparation of 2-cyano-8-methyl-4-oxo-4H-1-benzopyran

When the amide of Example 12, Step 4 is replaced with 2-carbamyl-8-methyl-4-oxo-4H-1-benzopyran, 2-cyano-8- methyl-4-oxo-4H-1-benzopyran is obtained which is used directly in the next step.

Step 3: Preparation of 8-bromomethyl-2-cyano-4-oxo-4H-1-benzopyran

When the benzopyran in Example 12, Step 5 is replaced with 2-cyano-8-methyl-4-oxo-4H-1-benzopyran, 8-bromomethyl-2-cyano-4-oxo-4H-1-benzopyran is obtained.

Step 4: Preparation of 2-cyano-8-(4-(quinolin-2-ylmethoxy)phenoxymethyl)-4-oxo-4H-1-benzopyran 1.0 g of 2-(4-hydroxyphenoxy)methylquinoline, 1.0 g of 8-bromomethyl-2-cyano-4-oxo-4H-1-benzopyran and 0.5 g of potassium carbonate are stirred at room temperature in 5 ml of dimethylformamide for 2 days. The reaction mixture is diluted with ethylacetate, filtered and concentrated. The residue is chromatographed on silica gel to give 0.45 g of 2-cyano-8-(4-(quinolin-2-ylmethoxy)phenoxymethyl)-4-oxo-4H-1-benzopyran.

Step 5: Preparation of 5-(8-(4-(quinolin-2-ylmethoxy)phenoxymethyl)- 4-oxo-4H-1-benzopyran-2-yl)tetrazole When the nitrile of Example 12, Step 7 is replaced with the cyano product from Example 33, Step 4 above, 5- 8-(4-(quinolin-2-ylmethoxy)phenoxymethyl)-4-oxo-4H-1- benzopyran-2-yl)tetrazole is obtained; m.p. >250° C.

EXAMPLE 34

5-(7-(3-(quinolin-2-ylmethoxy)phenoxymethyl)-4-oxo-4H-1-benzopyran-2-yl)tetrazole Step 1: Preparation of 2-cyano-7-(3-(quinolin-2-ylmethoxy)phenoxymethyl)-4-oxo-4H-1-benzopyran 1.5 g of 7-bromomethyl-2-cyano-4-oxo-4H-1-benzopyran and 1.5 g of the sodium salt of 2-(3-hydroxyphenoxy)methylquinoline are combined in 10 ml of dimethylsulfoxide and stirred at room temperature for 5 hours. The mixture is poured into water and extracted with methylene chloride. The organic solution is dried and evaporated. The residue is recrystallized from ethyl acetate/dimethylformamide to give 0.72 g of 2-cyano-7-(3-(quinolin-2- ylmethoxy)phenoxymethyl)-4-oxo-4H-1-benzopyran.

Step 2: Preparation of 5-(7-(3-(quinolin-2-ylmethoxy)phenoxymethyl)-4-oxo-4H-1-benzopyran-2-yl)tetrazole 0.72 g of 2-cyano-7-(3-(quinolin-2-ylmethoxy)-phenoxymethyl)-4-oxo-4H-1-benzopyran, 0.54 g of sodium azide and 0.96 g pyridinium chloride are combined in 20 ml of dimethylformamide and heated for 3 hours at 100° C. The mixture is poured into water and the precipitate filtered off. This crude product is recrystallized from dimethylformamide to give 5-(7-(3-(quinolin-2-ylmethoxy)phenoxymethyl)-4-oxo-4H-1-benzopyran-2-yl)tetrazole; m.p. 246° C.

EXAMPLE 35

2-carboxy-7-(4-(quinolin-2-ylmethoxy)phenoxymethyl)-4-oxo-4H-1-benzopyran

Step 1: Preparation of 7-bromomethyl-2-carboethoxy-4-oxo-4H-1-benzopyran

When 2-carboethoxy-7-methyl-4-oxo-4H-1-benzopyran is substituted for the cyano compound in Example 12, Step 5, 7-bromomethyl-2-carboethoxy-4-oxo-4H-1-benzopyran is obtained.

Step 2: Preparation of 2-carboethoxy-7-(4-(quinolin-2- ylmethoxy)phenoxymethyl)-4-oxo-4H-1-benzopyran 0.8 g of 2-(4-hydroxyphenoxy)methylquinoline, 0.99 g of 7-bromomethyl-2-carboethoxy-4-oxo-4H-1-benzopyran and 0.44 g of potassium carbonate are combined in 15 ml of dimethylformamide and heated at 70° C. for 18 hours. The mixture is poured into water and the aqueous mixture extracted with ethyl acetate. The organic solution is dried and evaporated and the resulting crude product is purified by column chromatography on silica gel to give 0.9 g of 2-carboethoxy-7-(4-(quinolin-2-ylmethoxy)phenoxy-methyl)-4-oxo-4H-1-benzopyran.

Step 3: Preparation of 2-carboxy-7-(4-(quinolin-2yl-methoxy)phenoxymethyl)- 4-oxo-4H-1-benzopyran When 2-carboethoxy-7-(4-(quinolin-2-ylmethoxy)-phenoxymethyl)- 4-oxo-4H-1-benzopyran is substituted for the ester in Example 21, 2-carboxy-7-(4-(quinolin-2ylmethoxy)phenoxymethyl)-4-oxo-4H-1-benzopyran is obtained; m.p. 216°-19° C.

EXAMPLE 36

5-(8-(4-(quinolin-2-ylmethoxy)benzoylamino)-4-oxo-4H-1-benzopyran-2-yl)tetrazole 5-(8-(3-(quinolin-2-ylmethoxy)benzoylamino)-4-oxo-4H-1-benzopyran-2-yl)tetrazole 5-(8-(2-(quinolin-2-ylmethoxy)benzoylamino)-4-oxo-4H-1-benzopyran-2-yl)tetrazole Step 1: Preparation of 2-carbamyl-8-nitro-4-oxo-4H-1-benzopyran When 2-carboethoxy-8-nitro-4-oxo-4H-1-benzopyran is substituted for the ester in Example. 12, Step 3, 2-carbamyl-8-nitro-4-oxo-4H-1-benzopyran is obtained.

Step 2: Preparation of 2-cyano-8-nitro-4-oxo-4H-1-benzopyran

When 2-carbamyl-8-nitro-4-oxo-4H-1-benzopyran is substituted for the amide in Example 12, Step 4, 2-cyano- 8-nitro-4-oxo-4H-1-benzopyran is obtained.

Step 3: Preparation of 5-(8-nitro-4-oxo-4H-1-benzopyran-2-yl)tetrazole

When 2-cyano-8-nitro-4-oxo-4H-1-benzopyran is substituted for the cyano compound in Example 35, Step 2, 5-(8-nitro-4-oxo-4H-1-benzopyran-2-yl)tetrazole is obtained.

Step 4: Preparation of 5-(8-amino-4-oxo-4H-1-benzopyran-2-yl)tetrazole 1.59 g of the nitro compound obtained in Example 36, Step 3, above, is suspended in 46 ml of methanol to which 1 ml of concentrated hydrochloric acid, and 0.17 g of 5% palladium on carbon are added. The mixture is stirred under hydrogen at atmospheric pressure for 18 hours, filtered, and the filtrate concentrated in vacuo to 1.10 g 5-(8-amino-4-oxo-4H-1-benzopyran-2-yl)tetrazole.

Step 5: Preparation of 4-(quinolin-2-ylmethoxy)benzoic acid 5.00 g of methyl-4-(quinolin-2-ylmethoxy)benzoate is dissolved in 120 ml of ethanol and 90 ml of 1N sodium hydroxide and the mixture is stirred at room temperature for 4 days. The mixture is concentrated in vacuo to remove the ethanol. The residue is diluted with water, acidified to pH 6 and the resulting solid is filtered off and recrystallized from methanol to give 3.12 g 4-(quinolin-2-ylmethoxy)benzoic acid.

Step 6: Preparation of 4-(quinolin-2-ylmethoxy)benzoyl chloride 1.28 g of 4-(quinolin-2-ylmethoxy)benzoic acid, in 4.6 ml of oxalyl chloride and 3 drops of dimethylformamide are combined in 50 ml of methylene chloride. The mixture is refluxed for 30 minutes and then concentrated in vacuo to give 4-(quinolin-2-ylmethoxy)benzoyl chloride.

Step 7: Preparation of 5-(8-(4-(quinolin-2-ylmethoxy)benzoylamino)-4-oxo-4H-1-benzopyran-2-yl)tetrazole 1.4 g of 4-(quinolin-2-ylmethoxy)benzoyl chloride, as a solid, is added to a mixture of 1.05 g of 5-(8-amino-4-oxo-4H-1-benzopyran-2-yl)tetrazole, 14 ml of pyridine, 46 ml of methylene chloride and 30 ml of dimethylformamide at 0° C. This is stirred at 0° C. for 1 hour, then at room temperature for 2 days. The mixture is concentrated to remove methylene chloride and diluted with water. The resulting crude product is crystallized from methanol/ether to give 5-(8-(4-quinolin-2-ylmethoxy)-benzoylamino)4-oxo-4H-1-benzopyran-2-yl)tetrazole; m.p. 245°-47° C.

Step 8:

When methyl-3-(quinolin-2-ylmethoxy)benzoate or methyl-2-(quinolin-2-ylmethoxy)benzoate is substituted for methyl-4-(quinolin-2-ylmethoxy)benzoate in Example 12, Step 5, then 5-(8-(3-quinolin-2-ylmethoxy)benzoylamino)-4-oxo-4H-1-benzopyran-2-yl)tetrazole or 5-(8-(2-(quinolin-2-ylmethoxy)benzoylamino)-4-oxo-4H-1-benzopyran-2-yl)tetrazole, respectively, is obtained.

EXAMPLE 37

2-carboxy-5-hydroxy-3-(4-methoxyphenyl)-7-(4-quinolin-2-ylmethoxy)benzoyloxy)-4-oxo-4H-1H-benzopyran Step 1: Preparation of 2-carboethoxy-5-hydroxy-3-(4-methoxyphenyl)-7-(4-(quinolin-2-ylmethoxy)benzyloxy)-4oxo-4H-1-benzopyran 0.62 g of 2-(4-chloromethylphenoxy)methyl quinoline, 0.78 g of 2-carboethoxy-5,7-dihydroxy-4'-methoxy isoflavone and 0.31 g potassium carbonate are refluxed in 30 ml of acetone for 17 hours. The mixture was concentrated and the crude product purified by flash chromatography on silica gel and crystallized from toluene to give 2-carboethoxy-5-hydroxy-3-(4-methoxyphenyl)-7-(4-(quinolin-2- ylmethoxy)benzyloxy)-4-oxo-4H-1-benzopyran.

Step 2: Preparation of 2-carboxy-5-hydroxy-3-(4-methoxyphenyl)-7-(4-quinolin-2-ylmethoxy)benzyloxy)-4-oxo-4H-1H-benzopyran 0.14 g 2-carboethoxy-5-hydroxy-3-(4-methoxyphenyl)-7-(4-(quinolin-2-ylmethoxy)benzyloxy)-4-oxo-4H-1-benzopyran and 0.78 g sodium bicarbonate are combined in 7 ml of water and 7 ml of ethanol and refluxed overnight. The mixture is extracted with ether and the aqueous neutralized to pH6. The resulting solid is collected, dried to give 2-carboxy-5-hydroxy-3-(4-methoxyphenyl)-7-(4-(quinolin-2-ylmethoxy)benzyloxy)-4-oxo-4H-1H-benzopyran; m.p. 195°-96° C.

EXAMPLE 38

3-(7-(3-(quinolin-2-ylmethoxy)benzyloxy)-3,4-dihydro-2-methyl-4-oxo-2H-1-benzopyran-2-yl)propanoic acid Step 1: Preparation of ethyl 3-(3,4-dihydro-7-hydroxy-2-methyl-4-oxo-2H-1-benzopyran-2-yl)propanoate 10.0 g of 2.4 dihydroxy acetophenone and 5.6 of pyrrolidine are refluxed in 75 ml of toluene for 2 hours while removing water with a Dean-Stark trap. 15.2 g ethyl levulinate is added and refluxing continued for an additional 2 hours. The mixture is diluted with ethyl acetate and the solution washed with 1 molar hydrochloric acid, water and brine. The dried ethyl acetate solution is concentrated and the residue purified by chromatography on silica gel to give ethyl 3-(3,4-dihydro-7-hydroxy-2-methyl-4-oxo-2H-1-benzopyran-2-yl)propanoate as an oil which is used, without further purification, for the next step.

Step 2: Preparation of ethyl-3-(7-(3-(quinolin-2-ylmethoxy)benzyloxy)-3, 4-dihydro-2-methyl-4-oxo-2H-1-benzopyran-2-yl)propanoate 2.5 g of ethyl-3-(3,4-dihydro-7-hydroxy-2-methyl-4-oxo-2H-1-benzopyran-2-yl)propanoate, 3.1 g of 2-(3-chloromethylphenoxy)methylquinoline and 1.2 g potassium carbonate are combined in 25 ml of dimethylformamide and stirred at room temperature overnight, then at 60° C. for 4 hours. The reaction mixture is diluted with ethyl acetate and this solution washed with water, dried and concentrated. The residue is chromatographed on silica gel to give 2.6 g of ethyl-3-(7-(3-quinolin-2-ylmethoxy)benzyloxy)-3,4-dihydro-2-methyl-4-oxo-2H-1-benzopyran-2-yl)propanoate as an oil which is used, without further purification, for the next step.

Step 3: Preparation of 3-(7-(3-(quinolin-2-ylmethoxy)benzyloxy)- 3.4-dihydro-2-methyl-4-oxo-2H-1-benzopyran-2-yl)propanoic acid 2.6 g of ethyl-3-(7-(3-(quinolin-2-ylmethoxy)- benzyloxy)-3,4-dihydro-2-methyl-4-oxo-2H-1-benzopyran-2yl)propanoate and 1.02 g of lithium hydroxide hydrate are combined in 30 ml of methanol, 30 ml of tetrahydrofuran and 10 ml of water and stirred at room temperature for 3 hours. The solvent is removed by evaporation and the residue diluted with water and washed with ether. The pH of the aqueous portion is adjusted to 5 and the suspension extracted with ethyl acetate. The dried ethyl acetate solution is concentrated and the residue purified by chromatography on silica gel to give 0.85 g of 3-(7-(3- (quinolin-2-ylmethoxy)benzyloxy)-3,4-dihydro-2-methyl-4- oxo-2H-1-benzopyran-2-yl)propanoic acid; m.p. 152°-54° C.

EXAMPLE 39

When 2,4-dihydroxyacetophenone in Example 17, Step 1, is replaced by the compounds of Table IV, below, then the corresponding product is obtained:

TABLE IV

| |
| --- |
| 2,6-dihydroxyacetophenone |
| 5-bromo-2,6-dihydroxyacetophenone |
| 2,4-dihydroxy-3-methylacetophenone |
| 2,4-dihydroxy-3-ethylacetophenone |
| 2,5-dihydroxy-3-methylacetophenone |
| 3,5-dihydroxy-3-ethylacetophenone |

EXAMPLE 40

When the products of Example 11 are substituted for 2-(3-chloromethylphenoxy)methylquinoline, and the products of Example 39 or the compounds from Table V, below, are substituted for 2-cyano-7-hydroxy-4-oxo-4H-1-benzopyran in Example 17, Step 4, the corresponding product is obtained.

TABLE V 2-carboethoxy-7-hydroxy-4-oxo-4H-1-benzopyran
2-carboethoxy-6-hydroxy-4-oxo-4H-1-benzopyran
2-carboethoxy-7-hydroxy-8-propyl-4-oxo-4H-1-benzopyran
2-carboethoxy-6-chloro-5-hydroxy-4-oxo-4H-1-benzopyran

EXAMPLE 41

When the products obtained from Examples 5 and 6 are substituted for 2-(4-hydroxyphenoxy)methylquinoline in Example 31, Step 2, the corresponding product is obtained.

EXAMPLE 42

When the products obtained from Examples 5 and 6 are substituted for 2-(4-hydroxyphenoxy)methylquinoline in Example 33, Step 4, the corresponding product is obtained.

EXAMPLE 43

When the compounds from Table VI, below, are substituted for 8-bromomethyl-2-carboethoxy-4-oxo-4H-1-benzopyran in Example 41, the corresponding product is obtained.

TABLE VI 7-bromomethyl-2-carboethoxy-4-oxo-4H-1-benzopyran
6-bromomethyl-2-carboethoxy-4-oxo-4H-1-benzopyran
5-bromomethyl-2-carboethoxy-4-oxo-4H-1-benzopyran

EXAMPLE 44

2-carboethoxy-8-(4-(quinolin-2-ylmethoxy)-phenylsulfinylmethyl)-4-oxo-4H-1-benzopyran When 2-carboethoxy-8-(4-(quinolin-2-ylmethoxy)-phenylthiomethyl)-4-oxo-4H-1-benzopyran (from Example 41) is treated with one equivalent of m-chloroperbenzoic acid in methylene chloride, 2-carboethoxy-8-(4-(quinolin-2- ylmethoxy)phenylsulfinylmethyl)-4-oxo-4H-1-benzopyran is obtained.

EXAMPLE 45

2-carboethoxy-8-(4-(quinolin-2-ylmethoxy)- phenylsulfonylmethyl)-4-oxo-4H-1-benzopyran When the sulfoxide obtained in Example 44 is treated with an excess of m-chloroperbenzoic acid in methylene chloride, 2-carboethoxy-8-(4-(quinolin-2-ylmethoxy)-phenylsulfonylmethyl)-4-oxo-4H-1-benzopyran is obtained.

EXAMPLE 46

3-(4-(2-cyano-4H-1-benzopyran-7-ylmethoxymethyl)-4-(quinolin-2-ylmethoxy)phenoxy)propanoic acid Step 1: Preparation of 2-(4-benzoyloxy-3-hydroxymethylphenoxy)methylquinoline When 2-benzoyloxy-5-hydroxybenzyl alcohol is substituted for the alcohol in Example 7, then 2-(4- benzyloxy-3-hydroxymethyl-phenoxy)methylquinoline is obtained.

Step 2: Preparation of 2-(2-benzoyloxy-5-chloromethyl)methylquinoline

When 2-(4-benzoyloxy-3-hydroxymethylphenoxy)-methylquinoline is substituted for the quinoline in Example 10, then 2-(4-benzoyloxy-3-chloromethylphenoxy)methylquinoline is obtained.

Step 3: Preparation of 2-cyano-7-(2-benzoyloxy-5-(quinolin-2-ylmethoxy)benzyloxy)-4-oxo-4H-1-benzopyran When 2-(2-benzoyloxy-5-chloromethyl)methylquinoline is substituted for the quinoline in Example 17, Step 4, 2- cyano-7-(4-benzoyloxy-3-(quinolin-2-ylmethoxy)-benzyloxy)-4-oxo-4H-1-benzopyran is obtained.

Step 4: Preparation of 2-cyano-7-(2-hydroxy-5-(quinolin-2-ylmethoxy)benzyloxy)-4-oxo-4H-1-benzopyran When the ester from Example 46 Step 3, above, is substituted for the ester in Example 21, 2-cyano-7-(2-hydroxy-5-(quinolin-2-ylmethoxy)benzyloxy)-4-oxo-4H-1-benzopyran is obtained.

Step 5: Preparation of ethyl 3-(2-(2-cyano-4H-1-benzopyran-7-ylmethoxymethyl)-4-(quinolin-2-ylmethoxy)phenoxy)propanoate The hydroxy compound from Example 46 Step 4, above, is treated with ethyl-3-bromoproprionate in dimethylformamide in the presence of potassium carbonate. The mixture is poured into water, extracted with ethyl acetate and the ethyl acetate solution washed with water, dried, evaporated to give ethyl 3-(2-(2-cyano-4H-1-benzopyran-7- ylmethoxymethyl)-4-(quinolin-2-ylmethoxy)phenoxy)propanoate.

Step 6: Preparation of 3-(2-(2-cyano-4H-1-benzopyran-7-ylmethoxymethyl)-4-(quinolin-2-ylmethoxy)-phenoxy)propanoic acid When the above ester is substituted for the ester in Example 21, 3-(2-(2-cyano-4H-1-benzopyran-7-ylmethoxymethyl)-4-(quinolin-2-ylmethoxy)phenoxy)-propanoic acid is obtained.

EXAMPLE 47

5-(3-(2-(2-tetrazol-5-yl-4H-1-benzopyran-7-ylmethoxymethyl)-4-(quinolin-2-ylmethoxy)phenoxy)propyl)tetrazole Step 1: Preparation of ethyl-3-(2-(2-tetrazol-5-yl-4H-1- benzopyran-7-ylmethoxymethyl)-4-(quinolin-2-ylmethoxy)phenoxy)propanoate When the cyano compound obtained in Example 46, Step 5, above, is substituted for the cyano compound in Example 12, Step 7, ethyl-3-(2-(2-tetrazol-5-yl-4H-1-benzopyran-7- ylmethoxymethyl)-4-(quinolin-2-ylmethoxy)phenoxy)propanoate is obtained.

Step 2: Preparation of 3-(2-(2-tetrazol-5-yl-4H-1- benzopyran-7-ylmethoxymethyl)-4-(quinolin-2-ylmethoxy)phenoxypropanamide When the ester obtained in Example 47, Step 1, above, is substituted for the ester in Example 12, Step 3, 3-(2-(2-tetrazol-5-yl-4H-1-benzopyran-7-ylmethoxymethyl)-4- (quinolin-2-yl-methoxy)phenoxy)propanamide is obtained.

Step 3: Preparation of 3-(2-(2-tetrazol-5-yl-4H-1- benzopyran-5-ylmethoxymethyl)-4-(quinolin-2-ylmethoxy)phenoxy)propanonitrile When the amide obtained in Example 47, Step 2, above, is substituted for the amide in Example 12, Step 4, 3-(2-(2-tetrazol-5-yl-4H-1-benzopyran-7-ylmethoxymethyl)-4- (quinolin-2-ylmethoxy)phenoxy)-propanonitrile is obtained.

Step 4: Preparation of 5-(3-(2-(2-tetrazol-5-yl-4H-1-benzopyran-7-ylmethoxymethyl)-4-(quinolin-2-ylmethoxy)phenoxy)propyl)tetrazole When the cyano compound obtained in Example 47, Step 3, above, is substituted for the cyano compound in Example 12, Step 7, 5-(-3-(2-(2-tetrazol-5-yl-4H-1-benzopyran-7- ylmethoxymethyl)-4-(quinolin-2-ylmethoxy)phenoxy)propyl)tetrazole is obtained.

EXAMPLE 48

2-cyano-7-(1 hydroxy-2-((2-carboxyethyl)thio)-2-(3-quinolin-2-ylmethoxy)phenyl)ethyl-4-oxo-4H-1-benzopyran Step 1: Preparation of 2-cyano-7-(1.2-oxido-2-(3-(quinolin-2-ylmethoxy)phenyl)ethyl)-4-oxo-4H-1-benzopyran To a solution of 0.1 mole of 2-cyano-7-(2-(3- quinolin-2-yl-methoxy)phenyl)ethenyl)-4-oxo-4H-1-benzopyran in 300 ml of methylene chloride containing 5 g of sodium bicarbonate, at 10° C., is added 0.11 mole of m-chloroperbenzoic acid. The mixture is stirred at 10° C. for several hours, then at room temperature. The solution is filtered, the methylene chloride washed with sodium bisulfite solution, potassium carbonate solution, then dried and evaporated in vacuo to give 2-cyano-7-(1,2-oxido-2-(3-(quinolin-2-ylmethoxy)phenyl)ethyl)-4-oxo-4H-1- benzopyran.

Step 2: Preparation of 2-cyano-7-(1-hydroxy-2-((2-carbomethoxyethyl)thio)-2-(3-(quinolin-2-ylmethoxy)-phenyl)ethyl)-4-oxo-4H-1-benzopyran 0.08 mole of the epoxide obtained in Example 48, Step 1, above, is stirred with 0.08 mole of methyl 3-thiolpropionate in 300 ml of methylene chloride at room temperature. The solvent is removed in vacuo and a mixture of the two isomers, 2-cyano-7-(I-hydroxy-2-((2-carbomethoxyethyl)thio)-2-(3-(quinolin-2-ylmethoxy)-phenyl)ethyl)-4-oxo-4H-1-benzopyran and 2-cyano-7-(2-hydroxy-1-((2-carbomethoxyethyl)thio-2-(3-(quinolin-2- ylmethoxy)phenyl)ethyl)-4-oxo-4H-1-benzopyran, is obtained. The isomers are separated by flash chromatography.

Step 3: Preparation of 2-cyano-7-(1-hydroxy-2-((2-carboxyethyl)thio)-2-(3-quinolin-2-ylmethoxy)phenyl)ethyl)-4-oxo-4H-1-benzopyran When the ester obtained in Example 48, Step 2, above, is substituted for the ester in Example 21, 2-cyano-7-(1- hydroxy-2-((2-carboxyethyl)thio)-2-(3-quinolin-2- ylmethoxy)phenyl)ethyl)-4-oxo-4H-1-benzopyran is obtained.

EXAMPLE 49

2-cyano-7-(2-hydroxy-1-((2-carboxyethyl)thio)-2-(3-quinolin-2-ylmethoxy)phenyl)ethyl)-4-oxo-4H-1-benzopyran When the isomer of the ester obtained in Example 48, Step 2, which is also obtained in Example 48, Step 2, is substituted for the ester in Example 48, Step 3, 2-cyano7-(2-hydroxy-1-((2-carboxyethyl)thio)-2-(3-quinolin-2-ylmethoxy)phenyl)ethyl)-4-oxo-4H-1-benzopyran is obtained.

EXAMPLE 50

When the products obtained in Example 14 are substituted for the ethenyl compound in Example 48, Step 1, the corresponding products are obtained.

EXAMPLE 51

Methyl 2-(7-bromomethyl-4-oxo-4H-1-benzopyran-2-yl)acetate

Step 1: Preparation of benzal diacetate 47.9 g of benzaldehyde and 46.1 g of acetic anhydride are combined and 4 drops of phosphorus trichloride are added and the mixture allowed to stand overnight. The resulting solid is crystallized from petroleum ether-/ethyl ether to give 61.2 g of benzal diacetate.

Step 2: Preparation of 7-methyl-1,3-benzodioxane-4-one 61 g of benzal diacetate, 44.6 g of 4-methylsalicylic acid and 45 ml of acetic acid are combined and 5 drops of concentrated sulfuric acid are added and the mixture is heated under reduced pressure, allowing acetic acid to distill off. When the theoretical amount of acetic acid is collected (about 2.5 hours) the mixture is allowed to cool, diluted with ether and the ether solution washed with potassium carbonate solution, sodium bisulfite solution and dried over sodium sulfate. The ether is removed in vacuo and the resulting solid crystallized from ethyl acetate/hexane to give 7-methyl-1,3-benzodioxane-4-one.

Step 3: Preparation of methyl 5-(2-hydroxy-4-methylphenyl)-3.5-dioxopentanoate

To a solution of 41.6 mmol of lithium diisopropyl amide in tetrahydrofuran (formed by adding n-butyl lithium in hexanes to diisopropyl amine in THF) is added 2.4 g (20.8 mmole) of methylacetoacetate over 10 minutes at 0° C. After stirring for 30 minutes, 2.0 g of 7-methyl-1,3-benzodioxane-4-one is added and the mixture stirred for 30 minutes. 6 ml of acetic acid is added and the mixture diluted with ethyl acetate and filtered. The ethyl acetate solution is washed with diluted hydrochloric acid, water and dried over sodium sulfate. The ethyl acetate is removed in vacuo to give methyl 5-(2-hydroxy-2-methylphenyl)-3,5-dioxopentanoate.

Step 4: Preparation of methyl 2-(7-methyl-4-oxo-4H-1-benzopyran-2-yl)acetate

Methyl-5-(2-hydroxy-4-methylphenyl)-3,5-dioxopentanoate is dissolved in a saturated solution of hydrogen chloride in methanol and allowed to stand for 2 hours. The solution is evaporated and the crude product purified by flash chromatography on silica gel to give methyl 2-(7-methyl-4-oxo-4H-1-benzopyran-2-yl)acetate.

Step 5: Preparation of methyl 2-(7-bromomethyl-4-oxo-4H-1-benzopyran-2-yl)acetate When methyl-2-(7-methyl-4-oxo-4H-1-benzopyran-2-yl)acetate is substituted for the ester in Example 31, Step 1, methyl 2-(7-bromomethyl-4-oxo-4H-1-benzopyran-2-yl)acetate is obtained.

Step 6: Preparation of methyl 2-(7-(4-(quinolin-2-ylmethoxy)phenoxymethyl)-4-oxo-4H-1-benzopyran-2-yl)acetate When the bromomethyl product from Example 51, Step 5, is substituted for the bromomethyl compound in Example 31, Step 2, methyl 2-(7-((4-quinolin-2-ylmethoxy)phenoxymethyl)-4-oxo-4H-1-benzopyran-2-yl)acetate is obtained.

Step 7: Preparation of 2-(7-(4-(quinolin-2-ylmethoxy)phenoxymethyl)-4-oxo-4H-1-benzopyran-2-yl)acetamide When the ester in Example 17, Step 2, is replaced by the ester obtained in Example 51, Step 6, 2-(7-(4- (quinolin-2-yl-methoxy)phenoxymethyl)-4 oxo-4H-1-benzopyran-2-yl)acetamide is obtained.

Step 8: Preparation of 2-(7-(4-(quinolin-2-ylmethoxy)phenoxymethyl)-4-oxo-4H-1-benzopyran-2-yl)acetonitrile When the amide in Example 12, Step 4 is replaced by the amide obtained in Example 51, Step 9, 2-(7-(4-(quinolin-2-ylmethoxy)phenoxymethyl)-4-oxo-4H-1-benzopyran-2-yl)acetonitrile is obtained.

Step 9: Preparation of 5-((7-(4-(quinolin-2-ylmethoxy)phenoxymethyl)-4-oxo-4H-1-benzopyran-2-yl)methyl)tetrazole When the nitrile in Example 34, Step 2 is replaced by the nitrile obtained in Example 51, Step 8, 5-((7-(4-(quinolin-2-ylmethoxy)phenoxymethyl)-4-oxo-4H-1-benzopyran-2-yl)methyl)tetrazole is obtained.

EXAMPLE 52

Following the above examples, when a substituted 4oxo-4H-1-benzopyran is replaced by a substituted 2-oxo-2H-1-benzopyran then a corresponding product is prepared. Representative examples are shown below in Examples 53–57.

EXAMPLE 53

When 2-cyano-7-methyl-4-oxo-4H-1-benzopyran in the procedure of Example 12, Step 5 is replaced with 3-cyano7-methyl-2-oxo-2H-1-benzopyran then the product prepared is 5-(7-(2-(3-(quinolin-2-ylmethoxy)-phenyl)ethyl)-2-oxo-2H-1-benzopyran-3-yl)tetrazole.

EXAMPLE 54

When the products of Example 13 are substituted for 3-(quinolin-2-ylmethoxy)benzaldehyde in Example 53, then the corresponding products are obtained.

EXAMPLE 55

When 2-cyano-7-hydroxy-4-oxo-4H-1-benzopyran in the procedure of Example 17, Step 4 is replaced with 3-cyano-8-hydroxy-2-oxo-2H-1-benzopyran then the products prepared are 3-cyano-8-(3-(quinolin-2-ylmethoxy)benzyloxy)-2-oxo2H-1-benzopyran and 5-(8-(3-(quinolin-2-ylmethoxy)benzyloxy)-2-oxo-2H-1-benzopyran-3-yl)tetrazole.

EXAMPLE 56

When 2-((3-chloromethylphenoxy)methyl)quinoline in Example 52 is replaced by 2-((4-chloromethylphenoxy)methyl)quinoline then the product prepared is 5-(8-(4- quinolin-2-ylmethoxy)benzyloxy)-2-oxo-2H-1-benzopyran-3-yl)tetrazole.

EXAMPLE 57

When 2-cyano-8-methyl-4-oxo-4H-1-benzopyran of Example 33, Step 3 is replaced with 3-cyano-7-methyl-2- oxo-2H-1-benzopyran then the corresponding products are obtained.

EXAMPLE 58

Following the above procedures the following products are prepared: 8-[3-(7-chloro-2-quinolinylethenyl)-benzyloxy]coumarin-3-carboxylic acid; 8-[3-(quinolin-2-ylmethoxy)benzyloxy]coumarin-3-carboxylic acid; and 8-[4- (quinolin-2-ylmethoxy)benzyloxy]coumarin-3-carboxylic acid.

We claim:
1. A compound of the formula:

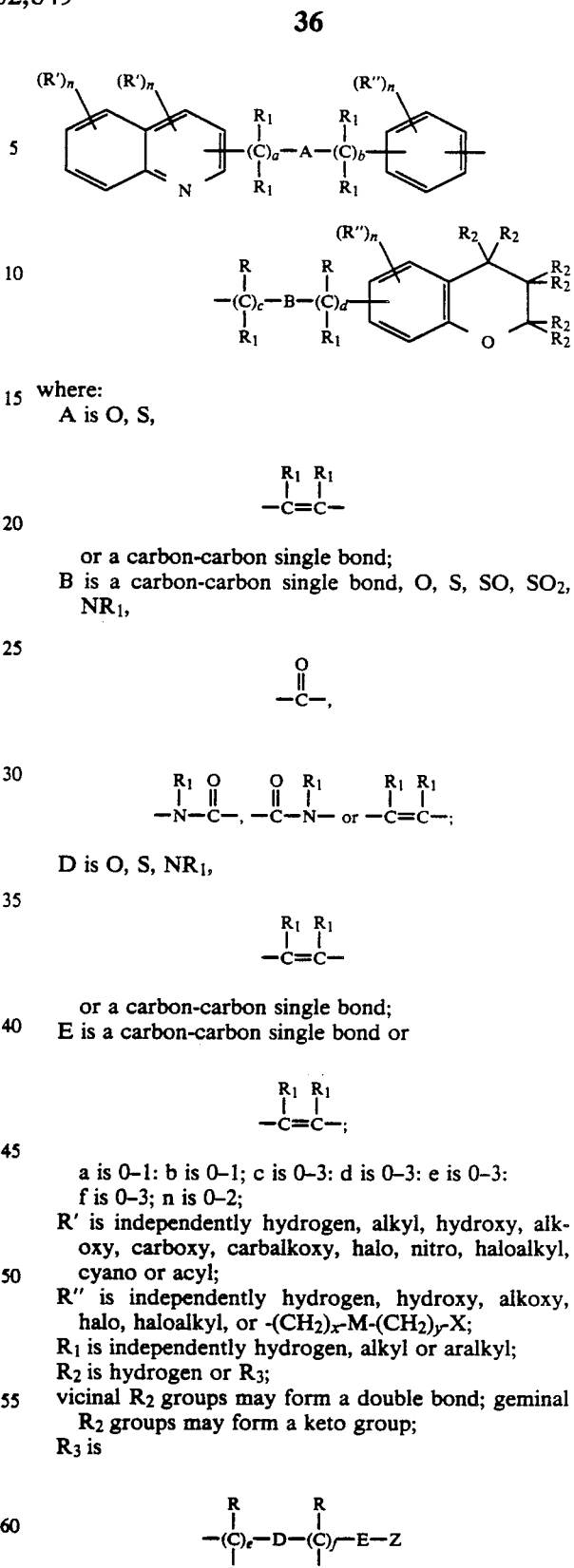

where:
A is O, S, $$-\underset{R_1}{\overset{R_1}{C}}=\underset{}{\overset{}{C}}-$$

or a carbon-carbon single bond;
B is a carbon-carbon single bond, O, S, SO, SO$_2$, NR$_1$, $$-\overset{O}{\underset{}{C}}-,$$

$$-\underset{}{\overset{R_1}{N}}-\overset{O}{\underset{}{C}}-, \quad -\overset{O}{\underset{}{C}}-\underset{}{\overset{R_1}{N}}- \text{ or } -\underset{R_1}{\overset{R_1}{C}}=\underset{}{\overset{}{C}}-;$$

D is O, S, NR$_1$, $$-\underset{R_1}{\overset{R_1}{C}}=\underset{}{\overset{}{C}}-$$

or a carbon-carbon single bond;
E is a carbon-carbon single bond or $$-\underset{R_1}{\overset{R_1}{C}}=\underset{}{\overset{}{C}}-;$$

a is 0–1: b is 0–1; c is 0–3: d is 0–3: e is 0–3:
f is 0–3; n is 0–2;
R' is independently hydrogen, alkyl, hydroxy, alkoxy, carboxy, carbalkoxy, halo, nitro, haloalkyl, cyano or acyl;
R" is independently hydrogen, hydroxy, alkoxy, halo, haloalkyl, or -(CH$_2$)$_x$-M-(CH$_2$)$_y$-X;
R$_1$ is independently hydrogen, alkyl or aralkyl;
R$_2$ is hydrogen or R$_3$;
vicinal R$_2$ groups may form a double bond; geminal R$_2$ groups may form a keto group;
R$_3$ is $$-(\overset{R}{\underset{R_1}{C}})_e-D-(\overset{R}{\underset{R_1}{C}})_f-E-Z$$

provided at least one R$_2$ group and no more than two non-geminal R$_2$ groups are R$_3$ at the same time;
R is independently hydrogen or -(CH$_2$)$_x$-M-(CH$_2$)$_y$-X provided M and A or B are not geminal oxygen atoms;

x is 0-3; y is 0-3;

M is a carbon-carbon single bond, O, S or NR$_1$;

X is hydrogen, alkyl, alkenyl, cycloalkyl, aryl, aralkyl, hydroxy, alkoxy, aralkoxy, amino, mono- and di-alkylamino, aralkylamino, acylamino, —CONR$_1$R$_1$, —COOR, CN, tetrazolyl,

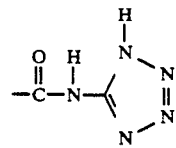

where R$_4$ is hydrogen, alkyl, haloalkyl, phenyl or benzyl;

vicinal R groups together may be -(CH$_2$)$_y$- where y is 1-4, thus forming a 3-6 membered ring;

geminal R$_1$ and R groups may together form a spiro substituent, -(CH$_2$)$_z$-, where z is 2-5;

geminal R$_1$ or R$_1$ and R groups may together form an alkylidenyl substituent,

Z is —COOR$_1$, —CN,

where R$_4$ is as described above,

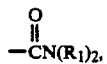

—OR$_1$, tetrazolyl, substituted tetrazolyl where the substituent may be alkyl, carboxyalkyl or carbalkoxyalkyl or

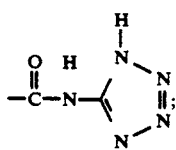

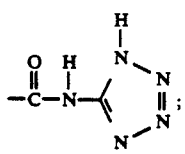

or a pharmaceutically acceptable salt thereof.

2. A compound of claim 1 where: one of R is -(CH$_2$)$_x$-X, -S-(CH$_2$)$_x$-X or -NR$_1$-(CH$_2$)$_x$-X; and/or one of R" is -CH$_2$R, R or -CH$_2$-O-(CH$_2$)$_x$-X and X is —CONR$_1$R$_1$, —COOR$_1$, —CN, tetrazolyl,

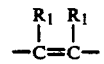

or acylsulfonamido.

3. A compound of claim 2 where: B is O, S, $$-\overset{R_1}{\underset{|}{C}}=\overset{R_1}{\underset{|}{C}}-$$

or a carbon-carbon single bond; Z is —COOR$_1$, —CON(R$_1$)$_2$, tetrazolyl or and R and R" are as described above.

4. A compound of claim 1 which is 5-(7-(3-(quinolin-2-ylmethoxy)benzyloxy)-4-oxo-4H-1-benzopyran-2-yl)tetrazole or a pharmaceutically accepted salt thereof.

5. A compound of claim 1 which is 5-(7-(3-(quinolin-2-ylmethoxy)phenoxymethyl)-4-oxo-4H-1-benzopyran-2-yl)tetrazole or a pharmaceutically accepted salt thereof.

6. A compound of claim 1 which is trans-(E)-5-(7-(2-(3(quinolin-2-ylmethoxy)phenyl)ethenyl)-4-oxo-4H-1-benzopyran-2-yl)tetrazole or a pharmaceutically accepted salt thereof.

7. A compound of claim 1 which is 5-(7-(2-(3-quinolin-2-ylmethoxy)phenyl)ethyl-)-4-oxo-4H-1-benzopyran-2-yl)tetrazole or a pharmaceutically accepted salt thereof.

8. A compound of claim 1 which is 2-carboxy-6-(3-(quinolin-2-ylmethoxy)benzyloxy)-4-oxo-4H-1-benzopyran-2-yl)tetrazole or a pharmaceutically accepted salt thereof.

9. A compound of claim 1 which is 2-carboxy-7-(3-(quinolin-2-ylmethoxy)benzyloxy)-4-oxo-4H-1-benzopyran-2-yl)tetrazole or a pharmaceutically accepted salt thereof.

10. A compound of claim 1 which is 3-(7-(3-(quinolin-2-ylmethoxy)benzyloxy)-3,4-dihydro-2-methyl-4-oxo-2H-1-benzopyran-2-yl)propanoic acid or a pharmaceutically accepted salt thereof.

11. A compound of claim 1 which is 5-(8-(4-(quinolin-2-ylmethoxy)benzoylamino)-4-oxo-4H-1-benzopyran-2-yl)tetrazole or a pharmaceutically accepted salt thereof.

12. A method for the treatment of hypersensitive ailments in humans and mammals comprising administering thereto an effective amount of a compound of the formula according to claim 1.

13. A pharmaceutical composition wherein the active ingredient is a compound according to claim 1 in admixture with a pharmaceutical carrier.

* * * * *

UNITED STATES PATENT AND TRADEMARK OFFICE
CERTIFICATE OF CORRECTION

PATENT NO. : 5,082,849
DATED : January 21, 1992
INVENTOR(S) : Huang et al.

It is certified that error appears in the above-identified patent and that said Letters Patent is hereby corrected as shown below:

On title page, insert the following:

* Notice: The portion of the term of this patent subsequent to December 11, 2007 has been disclaimed.

Signed and Sealed this

Twenty-second Day of March, 1994

Attest:

BRUCE LEHMAN

*Attesting Officer*   *Commissioner of Patents and Trademarks*